United States Patent [19]
Garby et al.

[11] Patent Number: 5,718,355
[45] Date of Patent: *Feb. 17, 1998

[54] INDICATOR DEVICE RESPONSIVE TO AXIAL FORCE FOR USE WITH INHALER

[75] Inventors: Gage Garby; Jeffery T. Ballas, both of Boulder, Colo.

[73] Assignee: Senetics, Inc., Boulder, Colo.

[*] Notice: The term of this patent shall not extend beyond the expiration date of Pat. No. 5,421,482.

[21] Appl. No.: 469,871

[22] Filed: Jun. 6, 1995

Related U.S. Application Data

[63] Continuation-in-part of Ser. No. 125,365, Sep. 22, 1993, Pat. No. 5,421,482, which is a continuation-in-part of Ser. No. 109,401, Aug. 19, 1993, Pat. No. 5,299,701, which is a continuation-in-part of Ser. No. 641,759, Jan. 17, 1991, abandoned, which is a continuation-in-part of Ser. No. 306,485, Feb. 3, 1989, Pat. No. 5,009,338.

[51] Int. Cl.⁶ .................... B67D 5/22; G09F 11/00
[52] U.S. Cl. .................... 222/36; 222/162; 215/230; 206/459.1; 116/285; 116/308; 116/318
[58] Field of Search .................... 206/534, 459.1, 206/459.5; 215/230; 128/200.23, 202.22, 205.23, 203.15; 116/308, 285, 311, 312, 318, 335; 222/32, 33, 36, 38, 402.11, 402.13

[56] References Cited

U.S. PATENT DOCUMENTS

| | | |
|---|---|---|
| 165,054 | 6/1875 | Baldwin . |
| 2,883,086 | 4/1959 | Davison et al. . |
| 2,953,242 | 9/1960 | Shaw .................... 206/534 |
| 3,085,745 | 4/1963 | Auberger . |
| 3,148,801 | 9/1964 | Radeloff et al. .................... 222/32 X |
| 3,419,187 | 12/1968 | Bazarnic . |
| 3,753,417 | 8/1973 | Garby . |
| 4,188,984 | 2/1980 | Lyall . |
| 4,347,853 | 9/1982 | Gereg et al. .................... 116/283 X |
| 4,354,621 | 10/1982 | Knickerbocker . |
| 4,565,302 | 1/1986 | Pfeiffer et al. .................... 222/32 X |
| 4,637,528 | 1/1987 | Wachinski et al. . |
| 4,668,218 | 5/1987 | Virtanen .................... 128/203.15 X |
| 4,756,423 | 7/1988 | Holtsch .................... 206/534 |
| 4,817,822 | 4/1989 | Rand et al. .................... 128/200.23 X |
| 4,890,572 | 1/1990 | Huang .................... 206/318 X |
| 4,969,578 | 11/1990 | Gander et al. . |
| 5,020,527 | 6/1991 | Dessertine .................... 128/200.23 |
| 5,174,473 | 12/1992 | Marelli .................... 222/38 |
| 5,209,375 | 5/1993 | Fuchs .................... 222/38 |
| 5,228,586 | 7/1993 | Fuchs .................... 222/38 |
| 5,261,548 | 11/1993 | Barker et al. .................... 215/230 |
| 5,289,946 | 3/1994 | Fuchs .................... 222/38 |
| 5,482,030 | 1/1996 | Klein .................... 116/308 X |

FOREIGN PATENT DOCUMENTS

| | | | |
|---|---|---|---|
| 1290484 | 9/1972 | United Kingdom | 128/200.23 |
| 2195544 | 4/1988 | United Kingdom | 128/200.23 |
| 86/02275 | 4/1986 | WIPO | 128/200.23 |

*Primary Examiner*—Allan N. Shoap
*Assistant Examiner*—Nathan Newhouse
*Attorney, Agent, or Firm*—Davis, Graham & Stubbs, LLP

[57] ABSTRACT

A device to indicate the application of a non-rotative force, having particular utility in recording the dispensing of a push-down activated aerosol medication dispenser. A non-rotative force on an outer cover is translated into a rotation of an indicator wheel relative to the outer cover by a set of flexible pawls engaged with a set of teeth. The pawls depress and thereby extend circumferentially when the applied force flexes them to effect a rotation of the teeth. Suitable means indicate the relative rotation of the teeth such as a window in the outer cover through which is visible indicia on the indicator wheel. The device may also include means to resist its operation by a child.

44 Claims, 10 Drawing Sheets

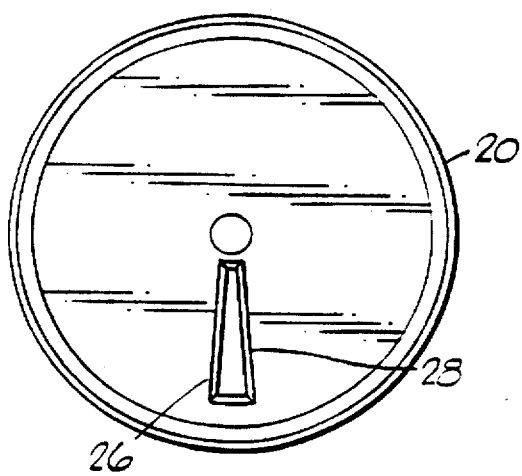
FIG.2
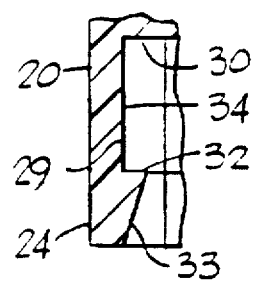
FIG.2A
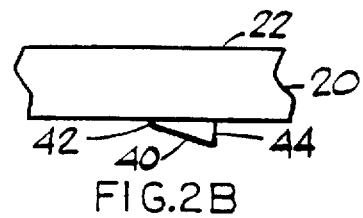
FIG.2B
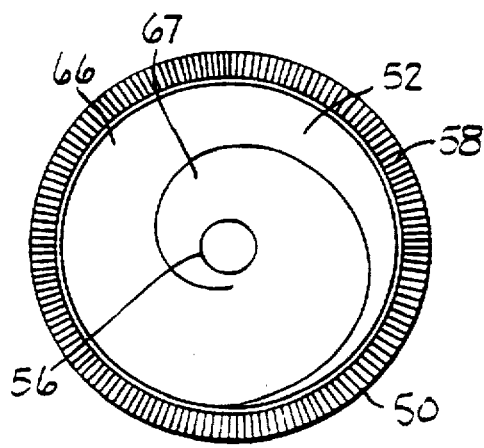
FIG.3
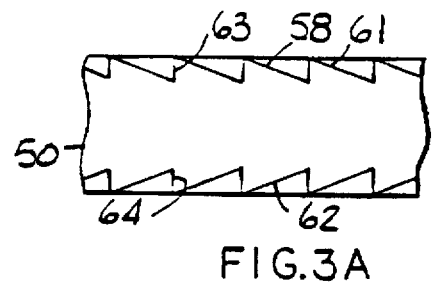
FIG.3A
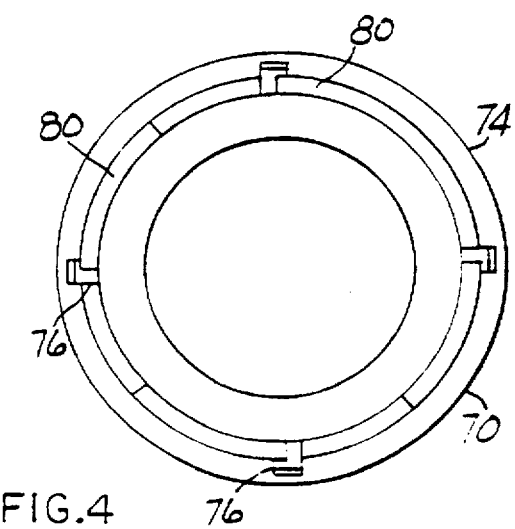
FIG.4
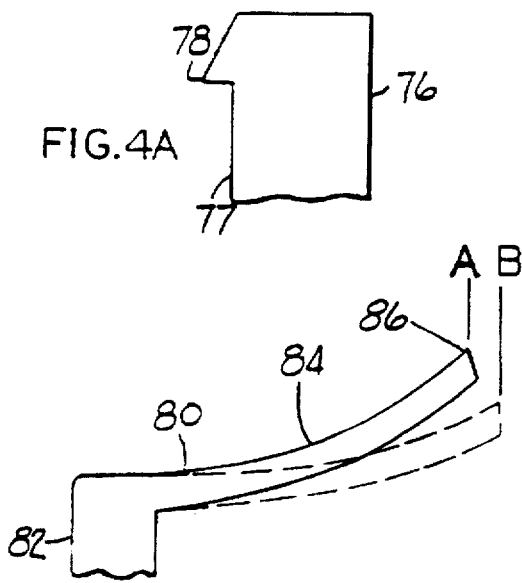
FIG.4A
FIG.4B

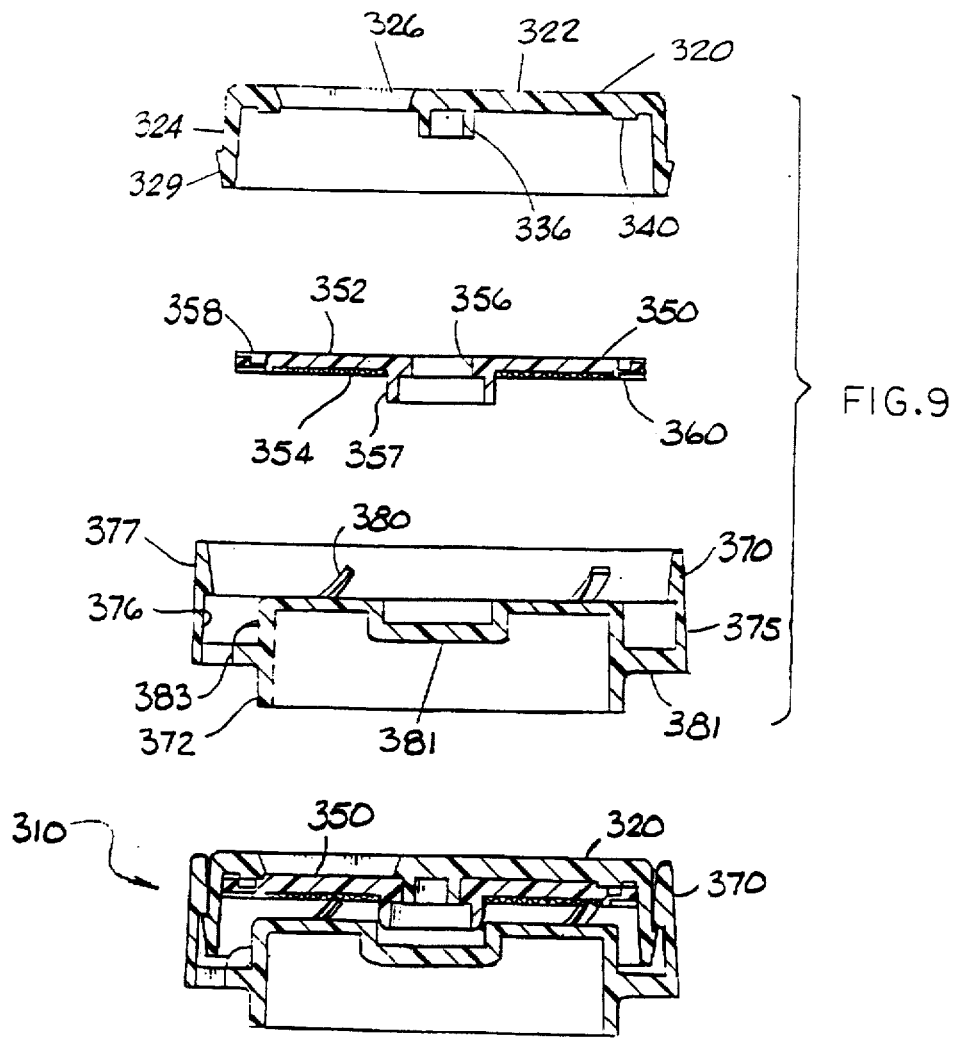
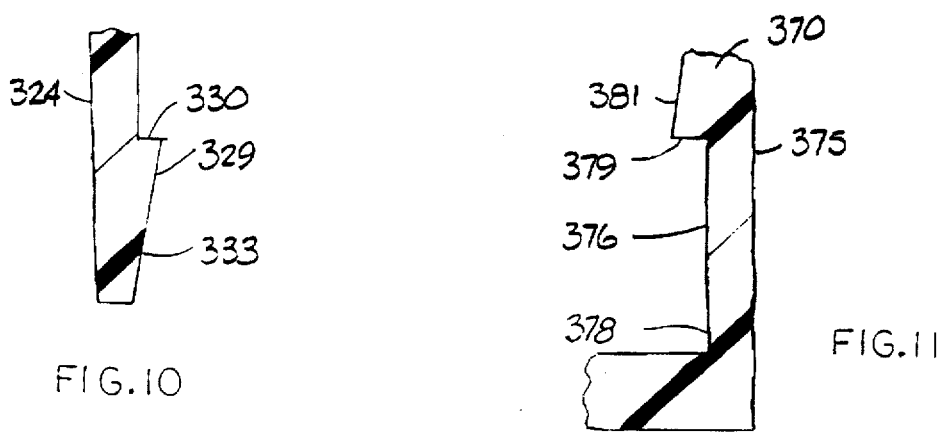

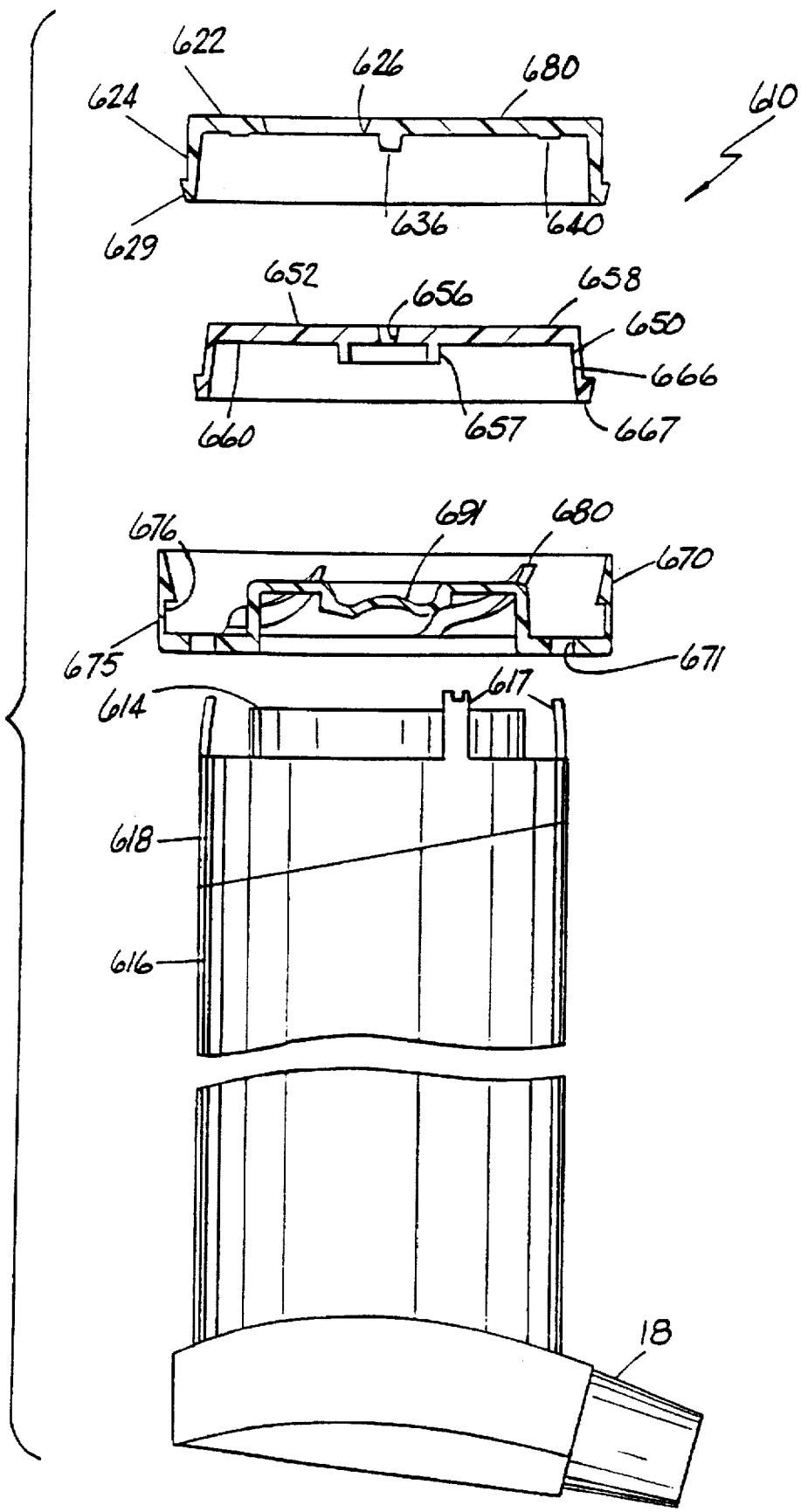

INDICATOR DEVICE RESPONSIVE TO AXIAL FORCE FOR USE WITH INHALER

This application is a continuation-in-part of application Ser. No. 08/125,365 filed Sep. 22, 1993, U.S. Pat. No. 5,421,482, which is a continuation-in-part of application Ser. No. 08/109,401 filed Aug. 19, 1993, U.S. Pat. No. 5,299,701, which is a continuation-in-part of application Ser. No. 07/641,759 filed Jan. 17, 1991, abandoned, which is a continuation-in-part of application Ser. No. 07/306,485 filed Feb. 3, 1989, U.S. Pat. No. 5,009,338.

BACKGROUND OF THE INVENTION

The present invention relates primarily to containers, bottles, dispensers, canisters and the like and, more particularly, to an indicator mechanism to indicate the number of times the container, bottle, dispenser or canister has been opened or used. The invention can also be used for any other application in which the number of times a given activity is performed must be indicated.

In the medical field, medical drugs have a predetermined therapeutic range in which the effects of taking the drug are beneficial. Under-utilization of a drug may endanger the user with the drug's side effects without reaching levels necessary for a therapeutic action. On the other hand, over-utilization may cause side effects or toxicity to a much greater extent than any possible benefit. Thus it is critically important that medication be administered in the correct amounts and at the correct times.

In the case of medication in the form of pills or tablets, a considerable number of pill-timing schemes have been used to solve the problem of reminding a patient to take a dose of medicine or reminding the patient that the patient has already taken the dose. The most used ones involve some scheme of compartmentalization of the necessary medication, such that the pills are placed in compartments that are labeled by day, dose number or time of day, or that are serially numbered. These devices are reasonably satisfactory only if a responsible person is available and has the time and patience to fill the compartments properly.

Some medication is not in the form of a pill or tablet at all, but is instead an aerosol. Such medication includes common asthma medication and other respiratory tract medication. These medications are often packaged as a liquid or a dry powder in a pressurized canister which releases a measured aerosol dose into the patient's mouth or nose upon activation. Of course, such medications are not amenable to packaging in numbered compartments.

A major concern with such medication delivery systems is that one cannot readily ascertain the amount of medication in the canister from time to time. Thus, the user may continue to operate the device as if to administer medication when, in fact, the canister is empty or holds only pressurized gas with no medication. In the prior art, this problem is addressed in a variety of ways, mostly inadequate. One of the most reliable and common methods of addressing this problem was the primitive method instructing the patient to immerse the canister in water periodically to see if it floats; if the canister floats, it is deemed empty.

This Background portion addresses both pill counting devices and aerosol devices, since those fields both relate to the recordation of medication administration. In the field of pill counting devices, a number of window-containing bottle caps have been invented. Through the window a movable element marked with an index is visible. Thus, by looking at the index mark displayed through the window, a user can see where in repetitive sequence of dose he or she is. One limitation to most such devices is that they are designed to operate only with closures that disengage from a container by application of a rotative force, such as threaded or bayonet-type closures. The devices generally do not operate with "press top" closures, closures that snap off from a container, or other devices in which the container, contents are accessed by the application of an axial force such as a push-actuated canister. Moreover, they are generally totally inapplicable to aerosol medication dispenser.

A serious disadvantage of prior art pill counting devices of the window indexing type is that there is no warning to the user in case the user does not turn the device far enough during the opening or closing to properly advance the window. Unless the user is alert to the index value before opening and then after closing such devices, the user will be unaware that the window failed to advance to a new index. Most users will not be this alert to the functioning of the device. In addition, most prior art devices fail to provide positive locking in both directions of movement; thus, the index may be moved appropriately when the device is opened or closed, but additional movement is not prevented when the device is moved in the opposite direction. This allows the index to drift, often causing failure or an incorrect reading, particularly after the device has been used over a period of time.

The device of U.S. Pat. No. 4,011,829 issued Mar. 15, 1977 to Wachsmann, et al., attempts to provide positive locking in both directions, but because of the direction of the tooth designed to prevent movement of the index upon closure, the device may not work reliably, particularly after wearing with use. Also, the device of Wachsmann does not provide space for the ratchet teeth to slide past the engagement teeth when the device is moving in a direction wherein such teeth should disengage, which may cause unreliable operation over a period of time. Another drawback of this device is its inclusion of a complicated "child proofing" feature with the indexing feature, which makes the device quite complex. Other features of this device, such as the method of providing the lost motion drive and the requirement of a post in the middle of the elements to hold the device together, also increase its complexity.

The device of U.S. Pat. No. 3,151,599 issued Oct. 6, 1964 to Livingston provides positive locking in both directions, but it does so by means of very closely spaced projections that would be difficult to manufacture economically. Furthermore, this device does not provide space for the projections to move while sliding past each other when not engaged.

The device of U.S. Pat. No. 4,666,051 issued May 19, 1987 to Trick has an indicator wheel with a serrated rim projecting above and below the plane of the wheel. The serrations engage mating serrations in upper and lower elements in order to drive the indicator mechanism. The serrations are rigid and, therefore, tend to wear excessively as they slide past one another.

The device of European Patent Application No. 87100917.2, published Jul. 27, 1987, by Schwab, has a cup-shaped exterior element that engages a frustoconical closure cap. The Schwab device is somewhat complicated in design and manufacture. The device of U.S. Pat. No. 4,220,247 issued Sep. 2, 1980 to Kramer also includes a cup-shaped exterior element which engages an inner element.

Other devices in the art include U.S. Pat. Nos. 4,511,050; by Nicol; 4,365,722 by Kramer; 4,749,093 by Trick; 4,782,966 by Thackrey; 4,753,189 by Mastman; 4,705,182 by Newel-Lewis; 4,662,520 by Griffen; 4,641,759 by Kelley; 4,634,012 by Kelley; 4,562,933 by Dennis; 4,528,933 by Allen; 4,511,050 by Nicol; 4,548,157 by Heroyah; 4,501,370 by Kelley; 4,489,834 by Thackrey; 4,432,300 by Lyss; 4,419,016 by Zoltan; 4,405,045 by Villa-Real; 4,357,192 by Moser; 4,347,804 by Villa-Real; 4,094,408 by Ford; 3,996,879 by Walton; 3,960,713 by Carey; 3,926,326 by Grau; 3,921,568 by Fish; 3,887,099 by Gillman; 3,753,417 by Garby; 3,446,179 by Bender; 3,334,731 by Dale; 2,943,730 by Tregilgas; 2,939,597 by Greene; 2,587,147 by Guion; 498,851 by Adsit; 4,500,005 by Forrester; 3,151,599 by Livingston; 4,666,051 by Trick; 4,345,541 by Villa-Real; 4,440,306 by Van Buskirk; 2,767,680 by Lermer; 4,723,673 by Tartaglia; 2,644,452 by Brown; 4,646,936 by Frazier; 3,766,882 by Babbitt; 3,977,554 by Costa; 5,011,032 by Rollman; 5,188,251 by Kusz; 5,184,739 by Kusz; and European Patent 0 230 323 by Schwab. More particularly in the field of aerosol medication dispensers, are U.S. Pat. Nos. 4,890,572 by Huang; 5,020,527 by Dessertine; 5,289,946 by Fuchs; 165,054 by Baldwin; 2,883,086 by Davison; 3,085, 745 by Auberger; 3,148,801 by Radeloff; 3,191,867 by Eelms; 3,419,187 by Bazarnie; 3,994,421 by Hansen; 4,291, 688 by Kistler; 4,354,621 by Knickerbocker; 4,565,302 by Pfeiffer; 4,637,528 by Wachinski; 4,756,423 by Holtsch; and 4,817,822 by Rand.

It is thus apparent from a review of this art that there is a need for an improved indicator cap that operates by application of an axial rather than rotative force. Preferably, such a device should provide positive controlled movement of the index on both opening and closing of the device, while also providing an indication to the user that the index has functioned properly each time the device is used. The basic design of such a device can also be used in other applications where it is necessary to have a record of the number of times a given event occurs.

Preferably, such a cap should have a minimum of parts, should be easily manufactured and assembled using standard injection molding and assembly methods, and should be usable with ordinary containers that are not necessarily specially designed for the cap.

SUMMARY OF THE INVENTION

The present invention is an indicator device with an indicator mechanism or an electronic indicator that advances by the application of an axial force. The indicator mechanism thus translates axial force into the rotation of an indicator symbol carrier in relation to a pointer or window. The device is particularly suited for use with aerosol-type medications which are administered by applying an axial force to a canister, or for use with medications that are kept in a container with a snap closure.

In broad terms, the advancement mechanism utilizes the axial force to move elements axially in relation to one another, and this relative axial movement is transformed into a rotation of an element in relation to another element by an indicator mechanism. The elements that move in relation to one another may be two in number, or some number greater than two. More specifically, the invention in a preferred embodiment includes an outer cover having a top and a depending skirt attached to the top; and a driver (sometimes referred to as a retainer or base herein). In a preferred embodiment, the driver nests in the outer cover. In another preferred embodiment, the outer cover nests in the driver so that only the top of the outer cover is exposed as an actuating "button." The invention also includes a rotational mechanism which may be separate from the outer cover and driver.

In the preferred embodiment, there is an indicator wheel which is positioned between the driver and the outer cover. The driver has several lugs which mate with several notches in the surface of the outer cover. Of course, the position of the lugs and notches may be reversed. The notches allow a measure of movement of the lugs in the axial direction, so that there is some play between the driver and the outer cover in the axial direction. These lugs and notches serve several functions in the preferred embodiment, although some or all of these functions may be performed by one or more substitute elements: the lugs and notches hold the driver and outer cover in engagement with one another; they limit the axial movement of the outer cover in relation to the driver; they establish a desired degree of preload on the pawls; they define the radial position of the outer cover in relations to the driver; they serve to allow "lost motion" of the elements as the outer cover is depressed in relation to the driver; and they define a "stop" to limit the degree of depression of the outer cover in relation to the driver if desired.

The indicator wheel has a set of teeth on one side which engage a set of flexible angled pawls on the driver, and a set of teeth on the other side which engage a set of outer cover teeth on the other side. The positions of the pawls and teeth on the respective elements may be reversed if desired. When an axial force is applied urging the outer cover and driver together, the outer cover and driver move toward one another slightly as the driver lugs move axially in the outer cover notches. The angled pawls in the driver flex toward the driver or "flatten out", which causes the driver pawl ends to shift slightly around the axis of the driver. This shift of the driver pawl ends, which are engaged with the indicator wheel teeth, drives the indicator wheel so as to rotate the indicator wheel relative to the driver notches. The rotation of the indicator wheel relative to the driver also results in rotation of the indicator wheel relative to the outer cover, since the engagement of the driver lugs with the outer cover notches ensure that the driver and outer cover are rotatively fixed.

The pawls preferably are curved rather than straight. The curvature enhances the circumferential or tangential displacement of the pawl tips as the indicator wheel depresses in relation to the driver and also helps define the amount of resistance to such depressing.

The side of the indicator wheel that is against the outer cover has indicia which are viewable through a window in the outer cover to indicate the progressive rotation of the indicator wheel as the axial force urging the outer cover and driver together is repeatedly applied. The indicia may be in the form of a sequence of numbers or, in the preferred embodiment, a spiral line or pattern which produces a "gauge" when viewed through the outer cover window. The gauge appears to decline in the window as the device is used repeatedly so as to progressively rotate the indicator wheel in relation to the outer cover. In this way, a record is kept of the total number of doses administered so that the user has some indication of whether an aerosol medication canister, for example, is being used up. Alternatively, the indicia on the indicator wheel may be numbers or symbols that record or limit the number of doses in a day; words such as "empty" or "full"; colors that vary as the medication is gradually exhausted; or any other varying indicia. The "window" may alternatively be in a skirt of the outer cover or driver.

When the axial force urging the outer cover and driver together is released, the driver pawls push the outer cover and driver apart. The device may also include a separate spring to urge the driver and outer cover apart. The separation of the driver and outer cover allows the driver pawl ends to flex away from the driver and to flee rotatively in the opposite rotative direction from the direction of rotation when the axial force was applied. This opposite rotative movement of the driver pawl ends causes the driver pawl ends to pass over a tooth of the indicator wheel, thereby "cocking" the mechanism for the next time an axial force is applied. This cocking and driving action causes the indicator wheel to advance by one tooth with each separate application of an axial force, and also produces an audible "click" to confirm the proper operation of the unit. The amount of axial force resisting the depression of the outer cover in relation to the driver depends on a number of factors, including the material, thickness and configuration of the pawls, the friction between the various slants, and the slope of the teeth.

As explained in the preceding paragraph, the cocking of the device is accompanied by the rotative movement of the driver pawl ends in relation to the indicator wheel teeth, so that the driver pawl ends pass over one of the indicator wheel teeth. During this cocking step, the indicator wheel is prevented from rotating by the engagement of the teeth that are on the opposite side of the indicator wheel with the teeth in the outer cover. Thus, the outer cover and driver do not rotate in relation to one another. The indicator wheel rotates in relation to both the outer cover and driver, in a single direction but not in the opposite direction. The engagement of the driver pawls with the teeth on one side of the indicator wheel produces the rotation of the indicator wheel in that single direction, while the engagement of the outer cover teeth with the teeth on the opposite side of the indicator wheel prevents rotation of the indicator wheel in the opposite direction during the cocking step. It is desirable that the rotation of the indicator wheel in relation to the outer cover upon depression of the outer cover in relation to the driver be somewhat greater than a single tooth but less than two teeth. This "overtravel" ensures proper advancement of the indicator wheel.

The invention thus provides a system to indicate the administration of medication through a medication container which is accessed by the application of an axial force, such as a canister-contained aerosol, or a snap closure or a "push-and-turn" type child-resistant closure on a vial for pills or capsules. In the case of a canister, the driver may be attached directly to the canister end with an adhesive or double-sided tape, or the driver may include a skirt which press-fits over the canister end, or the device may be attached to the canister or to a canister dispenser by other suitable means, including without limitation screw threads, snap fitting, bolts or pins. The device may also be integral with the canister end. The device may be used in any other application in which an indication of the occurrence of an event is desired. The device is incapable of advancing without applying the requisite axial force which accesses the medication, but it advances in precise and predetermined increments when that axial force is applied. It will be apparent that the device could be constructed to advance upon releasing the outer cover rather than upon depressing the outer cover.

An additional advantage to the invention is that it produces audible "clicks" to confirm that it is operating properly. When the axial force is applied to access the medication and thereby advance the indicator wheel, the indicator wheel teeth on the side adjacent the outer cover pass over the teeth of the outer cover to produce a "click" or "clicks" to confirm the advancement of the indicator wheel. When the axial force is released, the driver pawls pass over the teeth of the indicator wheel on the indicator wheel side adjacent the driver to produce a second "click" or "clicks" to confirm the proper "cocking" of the mechanism. It can be appreciated that the pawls and teeth producing the rotational displacement can be in a variety of locations on any of the several different elements of the mechanism. They may also be radially-extending rather than axially-extending.

One embodiment of the invention is configured so that medication cannot accidently be released, but can be released only when the device is properly assembled. This renders the device resistant to operation by children. One embodiment includes a gear reduction or other reduction system to translate an axial movement into a greater or lesser rotational displacement as may be desired in comparison to the preferred embodiment.

It can be appreciated that mechanisms other than the one disclosed in the preferred embodiment are possible for translating the axial force into a rotational force for advancement of the indicator. Also, the mechanism may be replaced entirely or partially with electronic components such as a button on the top of the medication canister which activates a switch when the button is pressed to release medication from the canister.

Other advantages of the invention include its simplicity of manufacture, assembly and operation, and its reliability.

BRIEF DESCRIPTION OF THE DRAWINGS

FIG. 2 is a top view of the outer cover of the invention.

FIG. 2A is a side sectional view of a portion of the outer cover of the invention.

FIG. 2B is a side sectional view of a portion of the outer cover of the invention.

FIG. 3 is a top view of the indicator wheel of the invention.

FIG. 3A is a side sectional view of a portion of the indicator wheel of the invention.

FIG. 4 is a top view of the driver of the invention.

FIG. 4A is a side sectional view of a portion of the driver of the invention.

FIG. 4B is a side sectional view of a portion of the driver of the invention.

FIG. 8 is a side sectional view of another embodiment of the invention.

FIG. 9 is an exploded side sectional view of the embodiment of FIG. 8.

FIG. 10 is a side sectional view of a detail of the embodiment of FIG. 8.

FIG. 11 is a side sectional view of another detail of the embodiment of FIG. 8.

FIG. 16 is a side sectional view of an alternate embodiment of the present invention.

DETAILED DESCRIPTION OF THE INVENTION

Figure 1:
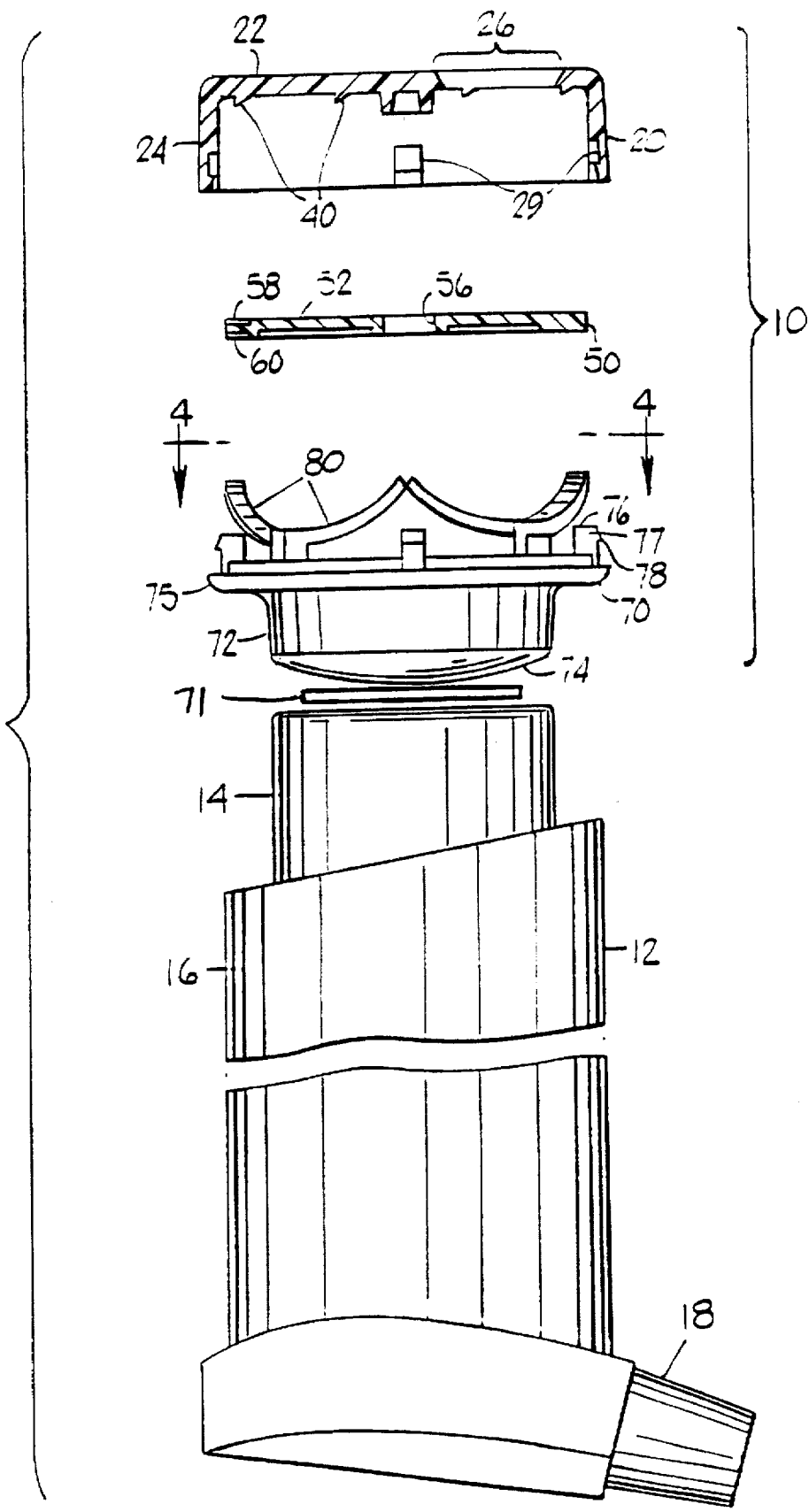
FIG. 1 is an exploded elevational view of the present invention with a canister and canister case.

An exploded elevational view of the invention 10 together with an ordinary canister aerosol medication dispenser 12 is shown in FIG. 1. The dispenser 12 includes a canister 14 which is housed in a canister case 16. Aerosol medication is dispensed from the canister 14 by grasping the canister case 16 and applying a force urging the canister 14 toward the canister case 16 to actuate a valve (not shown) in the canister 14, to release a measured dose of medication from the canister 14 and out the canister case outlet 18. The medication administered in this manner is typically respiratory tract medication such as asthma medication, and so the canister case outlet 18 is placed into the patient's mouth as the patient inhales. The system is quite reliable and simple to operate, and so it is often operated by the patient himself without the aid of a health care professional. Aerosol medication systems such as this are well known in the art, and will not be described in detail here.

The invention 10 includes three main elements in the preferred embodiment of FIG. 1: an outer cover 20, an indicator wheel 50, and a driver 70. The three elements are described in detail with reference to FIG. 1, as well as reference to FIGS. 2, 2A and 2B for the outer cover 20, FIGS. 3 and 3A for the indicator wheel, and FIGS. 4, 4A and 4B for the driver, and then the operation of the device is described with reference to the previously mentioned figures.

The outer cover includes a top 22 and an axially depending skirt 24 extending from the top. The axially depending skirt may flare radially outward slightly as it extends downward, in the manner shown, to facilitate the assembly and molding of the device. Through the top 22 is a window 26. As better shown in FIGS. 2 and 2A, the window 26 extends radially from near the center of the top to near the perimeter, and is of a width sufficient to allow the viewing of the indicia on the indicator wheel 50 in the manner described below. The edges 28 of the window 26 may be bevelled in the manner shown to improve the aesthetics of the device and reduce shadowing of the indicator wheel, or to improve the tactile aspects of the window for use with raised or depressed indicia (or braille symbols) on the indicator wheel that can be sensed in the dark or by the sight-impaired.

Spaced around the radially inner surface of the depending skirt 24 are a set of notches 29, which are better shown in the sectional view detail of FIG. 2A. Each notch 29 includes an upper wall 30 and a flat portion 34. A retainer 32 defines the lower end of the flat portion 34, and a bevelled portion 33 extends from the retainer to the bottom of the depending skirt 24. The circumferential width of the notch is just enough to receive the lugs 76 of the driver 70 described below without allowing any significant circumferential play between the notches 29 and those lugs 76. The lugs and notches of the preferred embodiment may be replaced with a slot and groove or a hole and post or any other arrangement allowing axial movement of the outer cover relative to the retainer.

In the center of the bottom surface of the top portion 22 of the outer cover 20 is an axially extending hub 36 which mates with a central hole 56 of the indicator wheel 50 in the manner described below. Also on the bottom surface of the top portion 22, around the periphery which meets the depending skirt 24, are a set of outer cover teeth 40 which engage the indicator wheel teeth 58 in the manner described below. The outer cover teeth 40, better shown in the sectional detail of FIG. 2B, include a ramp 42 on one side and a face 44 on the other side which engage the indicator wheel teeth 58 to produce a ratchet effect between the outer cover 20 and the indicator wheel 50 in the manner described below. It will be apparent that the mechanism for achieving this ratchet effect of preventing "wrong-way" rotation of the indicator wheel in relation to the outer cover could be a simple frictional engagement rather than the pawl and tooth arrangement described. Also, the pawl and tooth arrangement, or even the frictional engagement could be on the radially outer edge of the indicator wheel and the radially inner surface of the outer cover skirt, rather than the top of the indicator wheel and the bottom surface of the top portion of the outer cover.

The indicator wheel 50 is a disk-shaped element having an upper surface 52, a lower surface and a hole 56 through the middle. The diameter of the disk-shaped indicator wheel 50 is such that it nests into the outer cover 20. The upper surface 52 includes a set of indicator wheel upper teeth 58 around the periphery of the upper surface 52 as better shown in FIGS. 3 and 3A, and the lower surface includes a set of indicator wheel lower teeth 60 around the periphery of the lower surface.

The indicator wheel teeth 58 and 60 are shown best in the elevation detail of FIG. 3A. Both the teeth 58 on the upper surface 52 and the teeth 60 on the lower surface include a ramp portion 61 and 62, respectively, and a face portion 63 and 64, respectively. As explained in more detail below, the ramp portion 42 of the outer cover teeth 40 and the pawl ends 86 of the driver pawls 80 ride over the ramp portions 61 and 62 of the indicator wheel teeth 58 and 60 to allow rotation of the indicator wheel 50 in one direction in relation to the outer cover 20 and driver 70, while the pawl ends 86 of the driver pawls 80 and the faces 44 of the outer cover teeth 40 engage the faces 63 and 64 of the indicator wheel teeth 58 and 60 to prevent rotation of the indicator wheel 50 in the opposite direction in relation to the outer cover 20 and driver 70.

On the upper surface 52 of the indicator wheel 50 is a line which extends spirally from near the central hole 56 to near the radially inner edge of the upper teeth 58, in the manner shown in FIG. 3. Preferably, the surface 66 on one side of the line is one color and the surface 67 on the other side of the line is a different color; for example, the surface on one side can be red and the surface on the other side may be white. As the line dividing the differently colored surfaces 66 and 67 is presented for viewing through the window 26 of the outer cover 20 when the device is assembled, a kind of gauge results, as described in more detail below. The differing colors can be accomplished with the use of printing, painting, adhesive materials or other methods known in the art.

The driver 70 includes a circular base 72 with a bottom 74 configured to mate with the canister 14 of the canister aerosol medication dispenser 12. Such canisters typically have a concave end, and so the driver bottom on the preferred embodiment is convex as shown in FIG. 1 to mate with the canister concave end. The driver 70 is attached to the canister using a suitable driver mount such as the double-sided adhesive pad 71. The diameter of the base 72 is preferably about the same as the diameter of the canister 14, so that the base 72 can be pushed into the canister case 16 if necessary to actuate the canister valve. Other mounts are feasible such as a clamp or a buckle, or mounts that make the driver integral with the canister or mounts that make the device resistant to operation by a child. One such other mount —a press—fit mount—is described in connection with the alternate preferred embodiment described below.

Above the base 72 on the driver 70 is an annular ring 75 which holds several elements. The annular ring 75 is preferably of a diameter greater than the diameter of the base 72 and canister 14. This ensures that the canister end is not accessible to the user, so that the user must access the medication by applying a force to the device 10 to advance the indicator wheel 50 rather than by applying the force directly to the canister and thereby bypassing the device 10.

The annular ring 75 has a set of lugs 76 protruding upwardly. As better shown in the elevational detail of FIG. 4A, each lug 76 has a lug body 77, and a lug point 78 which engages the notches 29 of the outer cover 20 in the manner described below. The lug body 77 is somewhat flexible, so that it can flex radially inward as the lugs 76 pass over the bevelled portion 33 of the outer cover notches 29 when the driver 70 is assembled into the outer cover 20. The lug body 77 and the lug point 78 are dimensioned such that there is some axial play between the driver 70 and the outer cover 20; that is, the lugs 76 may extend all the way into the notches 29 so that the top of the lug body 77 is against the top wall 30 (see FIG. 2A) of the notch 29 while the outer cover 20 and driver 70 are positioned closely together, or the lugs 76 may be partially withdrawn from the notches 29 so that the lug point 78 is against the notch retainer 32 while the outer cover 20 and driver 70 are positioned farther apart.

Also extending upward from the annular ring 75 of the driver 70 is a set of driver pawls 80. Each driver pawl 80 includes a pawl base 82 and a curved flexible pawl body 84 which extends circumferentially and upwardly to terminate in a pawl end 86, all as better shown in FIG. 4B. The pawl end 86 engages the indicator wheel lower teeth 60 in a ratcheting manner whereby the pawl end passes over the ramp portion 62 of the indicator wheel lower teeth 60.

An important aspect of this embodiment of the invention is that the flexing of the pawls 80 produces an elongation of one of the dimensions of the pawl, as shown in the exaggerated depiction of FIG. 4B. The pawl may be configured in a curve so that it extends along the circumference of the circle defined by the radially outer edge of the driver 50, or it may be configured straight so that it extends tangentially with respect to that circle. The dimensions of the pawl that is thus elongated upon flexure is the circumferential or tangential dimension. The pawl in solid lines is relatively unflexed, while the pawl in dashed lines is relatively flexed. The unflexed position exists when the outer cover 20 and driver 70 are positioned apart, as when the driver lugs 76 are relatively withdrawn from the outer cover notches 29. In that position, the pawl end 86 is at circumferential position "A". The flexed position exists when the outer cover 20 and driver 70 are positioned together, as when the driver lugs 76 are fully positioned into the outer cover notches 29 against the notch top wall 30. In that position, the pawl end 86 is flexed downward by bending about the pawl base 82 and along the pawl body 84. The bending results in a shift in the pawl end 86 to position B, which is circumferentially spaced apart from position A. Because the pawl end 86 is engaged with the face 64 of the indicator wheel lower teeth 60 when the pawl 80 is in the relatively unflexed position corresponding to pawl end position A, the flexing of the pawl by the forcing together of the outer cover 20 and driver 70 and consequent shifting of the pawl end to position B forces the indicator wheel 50 to rotate the distance between position A and position B in relation to the driver 70.

When the force between the outer cover 20 and driver 70 is removed, the pawl unflexes to drive apart the outer cover 20 and driver 70. This unflexing allows the pawl end 86 to return to position A. The indicator wheel 50, however, does not rotate back to the earlier position where it was before the flexing because the pawl end is free to ride over the ramp portion 62 of the indicator wheel lower teeth 60. Moreover, the indicator wheel is prevented from rotating back to that earlier position by the one-way ratchet effect of the outer cover teeth 40 engaged with the indicator wheel upper teeth 58. As previously mentioned, the tooth and pawl position could be reversed, and a frictional engagement could replace the tooth and pawl arrangement used to prevent wrong-way rotation of the indicator wheel in relation to the outer cover.

The device 10 is preferably made by high-speed processes such as plastic injection molding. Once the molding of the three main pieces is completed, the pieces are assembled by hand or by automated assembly machines in any appropriate sequence, such as by nesting the indicator wheel 50 into the outer cover 20 and then forcing the driver lugs 76 into the outer cover notches 29, so that the driver lugs 76 are retained in the outer cover notches 29 by the notch retainer 32 or other retainer bearing against the lug points 78. When the lugs 76 are positioned in the notches 29, the driver pawls 80 are slightly flexed, or "preloaded" to provide a biasing force against the indicator wheel lower teeth 60. This biasing force holds the indicator wheel 50 against the outer cover 20 to maintain engagement of the indicator wheel upper teeth 58 with the outer cover teeth 40, maintains engagement of the pawl ends 84 with the indicator wheel lower teeth 60, and positions the outer cover 20 and driver 70 in their relatively apart position and ready for use. Alternatively, snap beads could be employed to hold the assembly together, such as a snap bead around the radially inner side of the bottom of the outer cover to hold the driver in place, or other means could be employed.

After assembly, the device 10 is attached to a medicine container such as the canister 14 shown in FIG. 1 or some other canister, vial, bottle or container, by use of double-sided adhesive tape or other suitable attachment means. The attachment means may include child-resistant elements so that the device is resistant to operation of the indicator mechanism, as well as the dispensing of medication, by a child.

The device is operated by applying an axial force urging the outer cover 20 toward the canister 14. The application of such force produces several kinds of movements, which may occur simultaneously with one another or in sequence in any order. One kind of movement is the actuation of the valve of the canister 14 to release a measured amount of aerosol medication from the canister and out the outlet 18 of the canister case 16. The other kind of movement produced by the application of an axial force urging the outer cover 20 toward the canister 14 is movement within the device 10. The axial force on the outer cover moves the combination of the outer cover 20 and indicator wheel 50 toward the driver 70, which causes the driver lugs 76 to shift upward in the outer cover notches 29 until the tops of the driver lugs 76 are against the upper wall 30 of the outer cover notches 29.

This second kind of movement—the moving together of the outer cover 20 and driver 70 caused by the axial force applied to the outer cover—also depresses the driver pawls 80, the ends 86 of which are engaged by the indicator wheel lower teeth 60. This depression—or flexing—of the driver pawls, as explained above, results in a circumferential or tangential lengthening of the pawls due to the pivoting of the pawl body 84 about the pawl base 82 and the flexing along the pawl body. FIG. 4B shows an exaggerated depiction of this circumferential or tangential lengthening of the pawl 80 from the unflexed position A (where the pawl 80 is shown in solid line) to the flexed position B (where the pawl 80 is shown in dashed lines). Because the pawl end 86 is engaged with the indicator wheel lower teeth 60, this circumferential or tangential lengthening of the driver pawls 80 drives the indicator wheel through the incremental circumferential distance of position A to position B, thus producing a rotation of the indicator wheel 50 relative to the driver 70. Because the pawls are flexible, this flexing may also produce flattening of the curvature in the pawls which also tends to lengthen them. The indicator wheel lower teeth 60 and driver pawls 80 are dimensioned such that this incremental circumferential shift is the length of a single tooth of the indicator wheel lower teeth 60.

The amount of circumferential or tangential travel of the driver pawls 80 is a function of several variables. Longer pawls tend to produce longer circumferential or tangential travel. Pawls with a large axial component to their direction tend to produce longer circumferential or tangential travel when flexed toward the driver. Also, locating the pawls radially inward will produce a greater rotation of the indicator wheel for the same amount of pawl travel.

It is noted that the rotation of the indicator wheel 50 does not translate into any rotation of the outer cover 20, because the outer cover 20 is rotationally fixed in relation to the driver 80 by the engagement of the driver lugs 76 in the outer cover notches 29.

Thus, the overall effect on the device 10 of applying an axial force urging the outer cover 20 toward the driver 70 is, one, the outer cover 20 shifts toward the driver 70 as the driver lugs 76 move upward in the outer cover notches 29 and, two, the indicator wheel 50 rotates counterclockwise in relation to the outer cover 20 and driver 70. This counterclockwise rotation of the indicator wheel 50 in relation to the outer cover 20 shifts to the window 26 of the outer cover 20 a new portion of the indicator wheel upper surface 52. With reference to FIG. 3, that new portion of the indicator wheel upper surface 52 is slightly clockwise from the upper surface 52 that was previously at the window 26. Because the upper surface 52 includes a spiral line or pattern as explained above and as shown in FIG. 3, which appears as a "gauge" when viewed through the window 26, the progressive rotational shift of the upper portion 52 viewable through the window has the effect of creating a declining or ascending line in the window. Thus, the repeated application of an axial force to the outer cover 20 gradually rotates the indicator wheel 50 to result in the appearance of a declining or ascending "gauge" in the window 26.

Referring again to the preferred embodiment of FIGS. 1–3B and 4–4B, the release of the axial force urging the outer cover 20 toward the canister 14, allows the flexed driver pawls 80 to unflex toward their natural relaxed position. This unflexing of the driver pawls forces the outer cover 20 and indicator wheel 50 away from the driver 80, so that the driver lugs 76 move downward in the outer cover notches 29 until the lug points 78 are stopped by the notch retainers 32 (see FIGS. 4A and 2A). The unflexing of the driver pawls 80 causes the pawl ends 86 to shift back to circumferential position A from circumferential position B. However, this circumferential shifting of the pawl ends 86 as the pawls 80 unflex does not produce any rotation of the indicator wheel 50. This is because the indicator wheel lower teeth 60 have a ramp 62 on one side and a face 64 on the other side (see FIG. 3A) to produce a one-way ratchet effect. The flexing of the pawls 80 when an axial force is applied urging the outer cover 20 toward the driver 70 causes the pawl ends 86 to shift circumferentially while engaged with the face 64 of the indicator wheel lower teeth 60 to drive the indicator wheel 50 through an incremental rotational movement. However, the release of that force and the consequential unflexing of the pawls 80 and circumferential shifting back to the pawl ends 86 does not rotate the indicator wheel 50 in the opposite direction, because the pawl ends 86 simply ride over the ramp portions 62 of the indicator wheel lower teeth 60, and because opposite direction rotation of the indicator wheel 50 is prevented by the engagement of the indicator wheel upper teeth 58 with the outer cover teeth 40.

This rotation of the indicator wheel 50 in relation to both the outer cover 20 and driver 80 has one other important effect. As the indicator wheel 50 rotates in relation to the outer cover 20, the outer cover teeth 40 ride over the indicator wheel upper teeth 58. More specifically, the ramp portions 42 of the outer cover teeth 40 ride over the ramp portion 61 of the indicator wheel upper teeth 58. The outer cover teeth 40 and indicator wheel upper teeth 58 are dimensioned such that the circumferential shift of the pawl ends 86 from position A to position B (see FIG. 4B) in the course of one cycle of applying an axial force urging the outer cover 20 toward the driver 80, causes the indicator wheel upper teeth 58 to shift one tooth in relation to the outer cover teeth 58. When the outer cover teeth 40 drop over the face 63 of the indicator wheel upper teeth 58 as this one-tooth shift occurs, an audible "click" results. This "click" confirms to the user that the indicator wheel has properly advanced.

The indicator wheel lower teeth 60, as mentioned above, are dimensioned such that the circumferential movement of the pawl ends 86 produced by applying or releasing an axial force to the outer cover 20, corresponds to one tooth. Therefore, the circumferential shift in the pawl ends 86 resulting from releasing the axial force on the outer cover 20, is equal to one tooth. The passing of the driver pawls 86 over the ramp portion 62 and over the face 64 of a tooth of the indicator wheel lower teeth 60, produces another audible "click". This "click", unlike the first "click" previously described, does not confirm any advancement of the indicator wheel 50, since the indicator wheel 50 does not advance at that time; rather, this "click" confirms that the driver pawls 80 have advanced by one tooth in the indicator wheel lower teeth 60, so that the driver pawls 80 will advance the indicator wheel 50 the next time an axial force is applied to the outer cover 20 to flex the driver pawls 86.

Although the description above indicates that the passing of the driver pawls over a set of teeth produces a "click", it should be recognized that actually there may be a set of several "clicks" of the four pawls to not pass over their respective teeth exactly simultaneously due to inexactness in the dimensions of the elements. In fact, there may be as many as four closely spaced "clicks" representing the four pawls passing over the teeth.

When the axial force is released from the outer cover 20 so that the driver pawls are permitted to unflex, the indicator wheel 50 is positively prevented from rotating back to its previous position before it was last advanced, by the engagement of the indicator wheel upper teeth 58 with the outer cover teeth 40. As described above, those sets of teeth 58 and 40 act as a one-way ratchet; rotation of the indicator wheel 50 is allowed in one direction as the ramp portion 42 of the outer cover teeth 40 ride over the ramp portion 61 of the indicator wheel upper teeth 58, but rotation of the indicator wheel 50 is prevented in the other direction by the engagement of the face 44 of the outer cover teeth 40 with the face 63 of the indicator wheel upper teeth 58.

The device 10 has been explained above in a preferred embodiment having teeth and pawls of certain elements and in certain positions. It will be apparent to those skilled in the art that some of these arrangements may be revised or reversed without departing from the scope or spirit of the invention. For example, without limitation, the teeth and pawls could be designed so that the indicator wheel advances when the force on the outer cover is released and the outer cover and driver separate, rather than when a force is applied and the outer cover and driver come together; the pawls could be on the indicator wheel and the engaged teeth on the driver rather than the other way around; the outer cover teeth and indicator wheel upper teeth could be reversed; and the pawls could be between the outer cover and the indicator wheel rather than between the indicator wheel and driver so that the pawls are positioned on the indicator wheel upper surface or the outer cover lower surface. It will also be apparent that the pawls and teeth on the various elements could be positioned on the outer circumference extending radially outward (or the inner circumference extending radially inward in the case of a disk having a center hole), rather than on the upper or lower surfaces extending downward or upward.

It should also be apparent from studying the drawings that the radial position of the pawls 80 is important in producing the desired amount of rotation of the indicator wheel. If the pawls are positioned toward the radially outer edge of the device, as shown in the figures, the circumferential shift in the pawl ends 86 produced by the flexing of the pawls 80 will result in a relatively small rotation of the indicator wheel. On the other hand, if the pawls are positioned toward the center of the device, the same amount of circumferential shift in the pawl ends 86 produced by the flexing of the pawls 80 will result in a relatively large rotation of the indicator wheel. Also, the degree of advancement of the indicator wheel is dependent on the distance that the outer cover moves toward and away from the retainer. This also relates to the length of the pawls, since a set of long pawls used for long distances between the outer cover and retainer will produce a greater advancement while a set of short pawls will produce a lesser advancement. Of course, the degree of advancement is also dependent on the curvature of the pawls and the geometry of the arrangement.

As previously mentioned, the upper surface 52 of the indicator wheel 50 may have indicia other than a spiral line to produce a declining or ascending line when viewed through the window 26, depending on the desired use of the device. For example, if it is desired to use the device to ensure that the patient takes a prescribed dose of medicine in prescribed time periods, and no more and no less, then the indicia may include abbreviations of the days of the week (such as Sa, Su, M, Tu, W, etc. for once a day medication or Sa1, Sa2, Su1, Su2, M1, M2, etc. for twice a day medication) arranged in a circle around the top surface 56. The teeth and pawls of the device are then dimensioned and configured such that each advancement of the indicator wheel 50 produced by applying a force urging the outer cover 20 toward the driver 70, advances one symbol under the indicator wheel. Thus the indicia visible through the window 26 successively advances through Sa, Su, M, Tu, W, etc. or Sa1, Sa2, Su1, Su2, M1, M2, etc. as the device is repeatedly operated. As another example, the indicator wheel 50 upper surface 52 may have a spiral line as indicia, but the spiral may be of such a configuration, and the teeth and pawls of the device of such a configuration and dimension, that the gauge produced by the viewing of a portion of the spiral line through the window moves through its entire range based not on the contents of the medication canister but on the allowable dosage in a day or in some other chosen time period. For example, if the medication is prescribed for discretionary as-needed administration to the patient, but not more than five times a day, then the gauge would go through its entire range with five doses dispensed. Thus, by a glance at the window, the user can determine how close he or she is to the maximum daily dose. At the outset of a new day, the gauge is reset.

The spiral line on the top of the indicator wheel 50 may go through approximately 360° as shown in FIG. 3 or any angle more or less than that. If the spiral line goes through less than 360°, then of course, the gauge goes through its entire range in something less than a full revolution of the indicator wheel relative to the outer cover. Thus, it would be necessary in that instance to reset the gauge to the starting position when the gauge indicates that the canister is empty and the next canister is started. If the spiral line is more than 360°, then two or more portions of the line may be visible at the same time through the window, and the user may have some difficulty in ascertaining which of the line portions is the correct one corresponding to the amount of medication remaining in the canister.

On the other hand, a spiral line that goes through more than 360° has the advantage of allowing for a gauge that "moves" in lesser increments than with a spiral line of 360° or less. This may be important because there is a practical limit to the number of teeth that can be engaged with the pawls of the device. While it is feasible to mold about 240 teeth onto the indicator wheel for engagement with the driver pawls, which corresponds to the number of doses in common canister-contained aerosol medication such as asthma medication, it may not be readily feasible to mold many more than 240 teeth onto a device having a convenient size. Therefore, common canister-contained medication that contains about 240 doses can be used with a device having 240 teeth so that each time the medication is administered, the indicator wheel rotates 1/240 of a full circle and the gauge declines from full to empty in one revolution of the indicator wheel. But if the canister contains, for example, 500 doses, then it is difficult to mold the necessary 500 teeth to produce a gauge that declines from full to empty in one revolution of the indicator wheel.

Figure 3B:
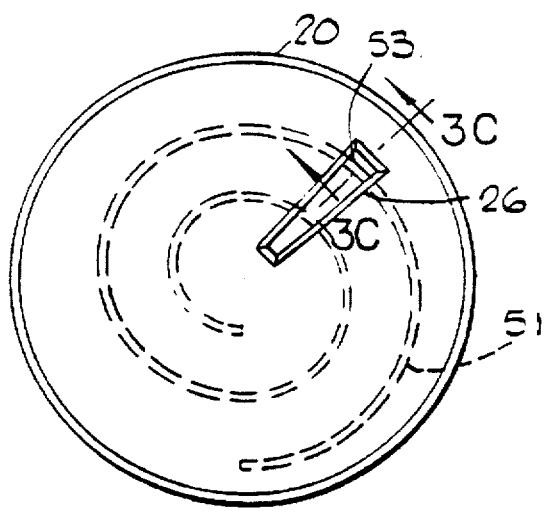
FIG. 3B is a top view of an alternate embodiment of the invention.
Figure 3C:
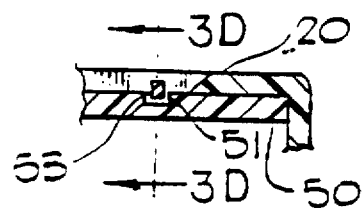
FIG. 3C is a side sectional view of an alternate embodiment of the invention, taken along line 3C—3C of FIG. 3B.
Figure 3D:
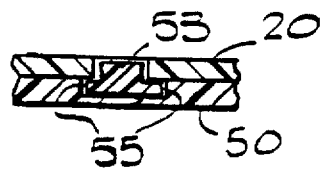
FIG. 3D is a side sectional view of an alternate embodiment of the invention, taken along line 3D—3D of FIG. 3C.

An approach to this problem is as shown in FIG. 3B which is a top view of the invention. The indicator wheel includes a spiral groove 51 which extends more than 360° (720° in the embodiment of FIG. 3B). The spiral groove 51 receives a small marker 53, better shown in FIG. 3C taken along line 3C—3C of FIG. 3B and FIG. 3D taken along line 3D—3D of FIG. 3C. The marker 53 is a small key that slidably fits into the spiral groove at the window 26. It is restrained from falling out of the spiral groove and the window 26 by a pair of ears 55 which extend along the spiral groove 51 under the outer cover 20. Thus, when the indicator wheel 50 rotates relative to the outer cover 20, the marker 53 slides in the spiral groove 51 and stays visible in the window 26. As the marker 53 slides in the spiral groove 51, it moves radially toward the center or perimeter of the outer cover 20, thereby acting as a gauge. Of course, the marker may be painted a distinctive color to aid in distinguishing it from the background of the indicator wheel 50 visible through the window 26. Also, the tabs of the marker may be flexible so that they can deform to allow the tab to be displaced back to the start position after reaching the end position.

It should also be appreciated that the spiral line or groove described above need not be a true geometric spiral. For example, the line or groove can be configured to move rapidly toward the center when it is near the periphery, and then slowly when it is near the center of the indicator wheel 50, so that the user has ample warning when the canister is running low.

Figure 7:
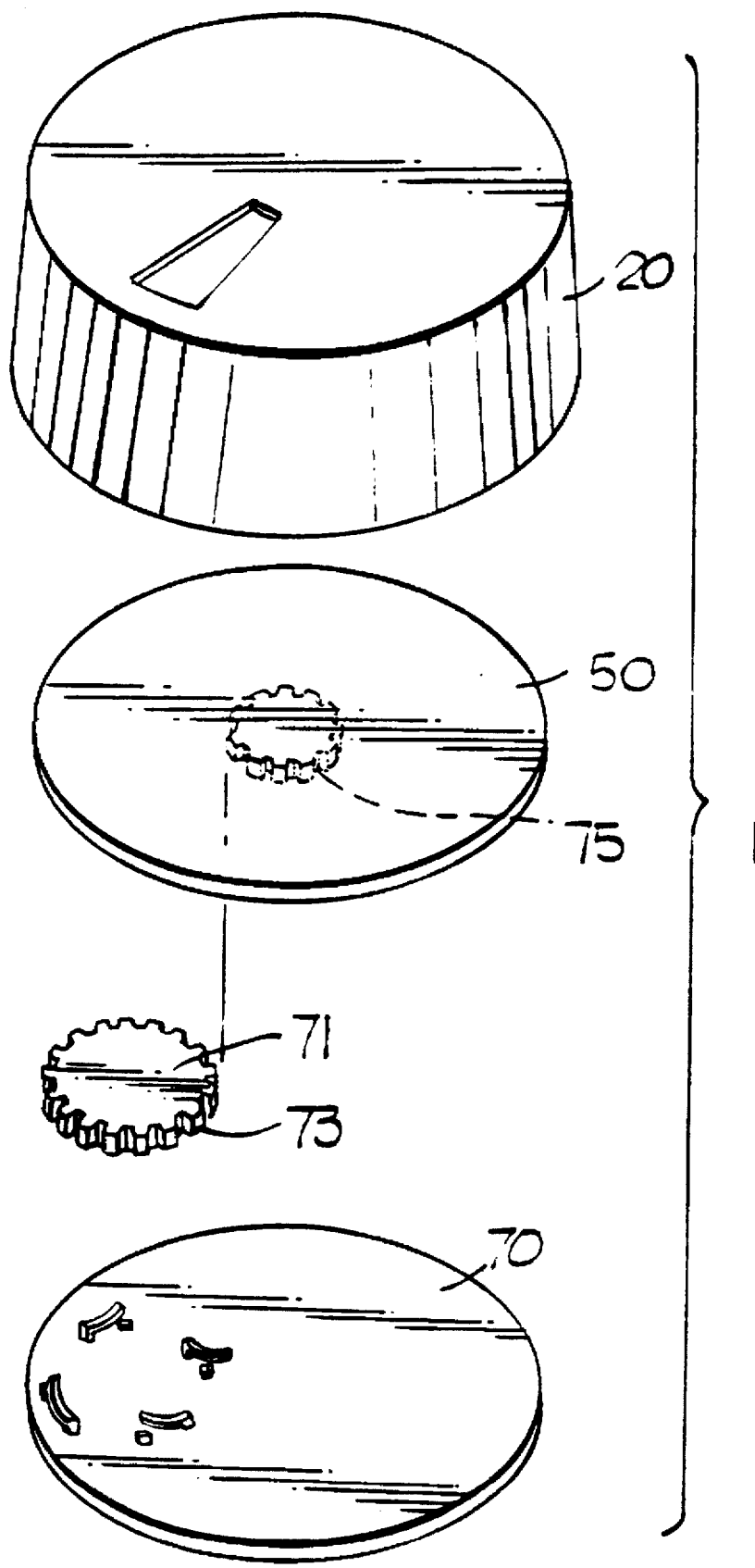
FIG. 7 is an exploded perspective view of an alternate embodiment of the present invention.

An opposite approach is shown in the exploded perspective view of FIG. 7 in which some details are omitted for clarity. This embodiment includes the already-discussed elements of a driver 70, an indicator wheel 50 and an outer cover 20. However, the driver pawls are arranged in a small circle on one side of the driver 70. Rather than bearing directly against a set of teeth on the indicator wheel 50, the pawls bear against a set of teeth on the bottom of a reduction wheel 71. The reduction wheel 71 has a set of reducing teeth 73 around its perimeter which engage a toothed hub 75 on the indicator wheel 50. It can be appreciated that the rotation of the reduction wheel 71 is increased when transferred to the indicator wheel 50, by the gear ratio of those two wheels. If, for example, the gear ratio is 10 to 1 and there are 200 teeth on the bottom of the reduction wheel 71 which are engaged one at a time by the pawls on the driver 70, then it will take 20 advances to turn the indicator wheel a complete revolution relative to the outer cover 20.

It should also be appreciated that the window of the preferred embodiment could be replaced with a hole in the outer cover and a hub in the indicator wheel extending into the hole so that it is visible through the outer cover. The hub has an arrow and the outer cover would then have a set of symbols arranged in a circle, or visa versa. Each time the indicator wheel rotates relative to the outer cover, the arrow points to a new symbol.

Figure 3E:
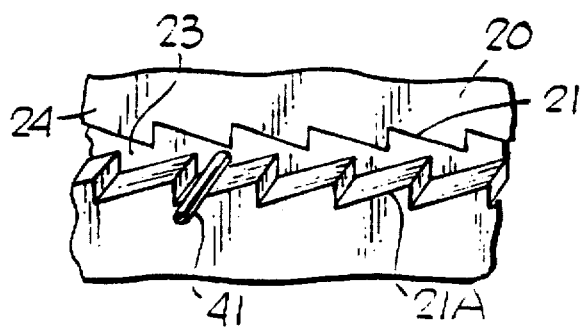
FIG. 3E is a partial perspective view of an alternate embodiment of a mechanism to advance the indicator wheel relative to the outer cover of the present invention.
Figure 3F:
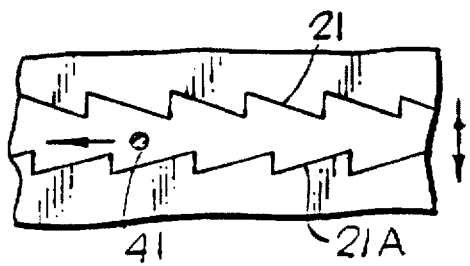
FIG. 3F is a partial side elevation view of the elements shown in FIG. 3E.

It is possible to use other mechanisms to translate the axial force applied to the outer cover to a rotation of the indicator wheel relative to the outer cover, such as the mechanisms shown in FIGS. 3E and 3F. FIG. 3E shows a partial perspective view of the inside of the depending skirt 24 of the outer cover 20, looking radially outward. The inside of the depending skirt 24 includes a radially extending groove 23 which goes completely around the depending skirt 24, although only a portion of the groove 23 and the depending skirt 24 are shown in the drawing of FIG. 3E for clarity. The top of the groove 23 is bounded by an upper set of teeth 21 and the bottom of the groove 23 is bounded by a lower set of teeth 21A. Disposed in the groove 23 between the upper set of teeth 21 and the lower set of teeth 21A is at least one engaging tab 41 which extends radially outward from the indicator wheel (not shown for clarity) into the groove 23. The engaging tab may be of any suitable cross-section, and the one in FIGS. 3E and 3F is of a circular cross-section.

In operation, the force applied to the top of the outer cover 20 to release medication, serves to move the outer cover 20 and the indicator wheel 50 together. This relative movement of the outer cover 20 and indicator wheel 50 together causes the engager tab 41 of the indicator wheel to ride along a ramp of a tooth of the upper set of teeth 21. Because the ramp is at an incline, the engager tab 41 rides down the ramp, which drives the indicator wheel 50 circumferentially to result in a rotation of the indicator wheel 50 relative to the outer cover 20. When the engager tab 41 is all the way to the bottom of the ramp, the outer cover 20 and indicator wheel 50 can move no closer together and the indicator wheel 50 cannot rotate any further relative to the outer cover. Medication has now been dispensed, and the force on the outer cover is released. The outer cover 20 then moves away from the indicator wheel 50 (which movement may be assisted by a flexible pawl or other spring-like element disposed between the outer cover 20 and the indicator wheel 50). The engager tab 41 moves across the width of the groove 23 and engages a ramp of a tooth of the lower set of teeth 21A. That ramp then serves to drive the engager tab 41 another increment circumferentially to effect another incremental rotation of the indicator wheel 50 relative to the outer cover 20. Thus, it can be seen that the indicator wheel 50 rotates relative to the outer cover 20 incrementally as a force in applied to the outer cover 20 and then incrementally again as the force is released from the outer cover 20. By arranging the indicia on the indicator wheel and dimensioning the teeth 21 and 21A appropriately, the device thus counts in a discernable fashion the dispensing of medication.

Figure 3G:
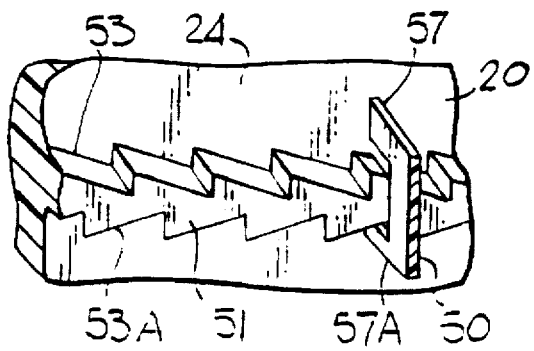
FIG. 3G is a partial perspective view of another alternate embodiment of a mechanism to advance the indicator wheel relative to the outer cover of the present invention.
Figure 3H:
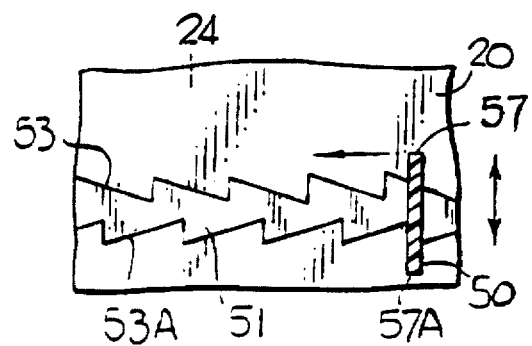
FIG. 3H is a side elevational view of the elements of FIG. 3G.

Yet another mechanism to translate the axial force applied to the outer cover to a rotation of the indicator wheel relative to the outer cover, is shown in FIGS. 3G and 3H. The general concept of this mechanism is similar to that shown in FIGS. 3E and 3F, in that it relies upon teeth having an inclined ramp and an engaging device which is driven circumferentially by the ramp. FIG. 3G is a partial perspective view of the inside of the depending skirt 24 of the outer cover 20, looking radially outward. The inside surface of the depending skirt includes a rib 51 extending radially inward. For clarity, only a portion of the rib 51 and the depending skirt 24 are shown, although it will be appreciated that the rib extends all the way around the depending skirt 24. The upper side of the rib 51 includes a set of upper teeth 53 and the lower side of the rib 51 includes a set of lower teeth 53A. The indicator wheel 50 has a pair of tabs, an upper tab 57 and a lower tab 57A. The upper tab 57 extends radially outward from the indicator wheel 50 above the rib 51 and the lower tab 57A extends radially outward from the indicator wheel 50 below the rib 51.

In operation, the force applied to the top of the outer cover 20 to release medication, serves to move the outer cover 20 and the indicator wheel 50 together. This relative movement of the outer cover 20 and indicator wheel 50 together causes the lower tab 57A of the indicator wheel 50 to ride on the ramp of a tooth of the lower set of teeth 53A of the rib 51. The riding of the lower tab 57A on the ramp incrementally rotates the indicator wheel 50 relative to the outer cover 20. When the lower tab 57A reaches the bottom of the ramp of the lower set of teeth 53A, the indicator wheel 50 and the outer cover 20 cannot move together any more, and the indicator wheel 50 cannot rotate any more in relation to the outer cover 20. When the force applied to the outer cover 20 is released, the outer cover 20 and indicator wheel 50 move apart (which movement, again, may be assisted by a flexible pawl or other spring-like element disposed between the indicator wheel 50 and the outer cover 20). This moving apart causes the upper tab 57 of the indicator wheel 50 to ride on the ramp of a tooth of the upper set of teeth 53 of the rib 51 of the indicator wheel 50. This riding of the upper tab 57 on the ramp produces another incremental rotation of the indicator wheel 50 relative to the outer cover 20.

Next described is an alternative embodiment for use with a different type of aerosol medication canister case. FIG. 5 shows the dispenser 112 with a canister case 116, a driver 170, an indicator wheel 150 and an outer cover 120. (For ease of reference, the 100-series labels of FIG. 5 generally correspond to the same labels of FIG. 1 without the first digit "1".) The canister case 116 is similar to the canister case 16 of the FIG. 1 previously described in that it has a canister case outlet 118 and a body to receive a canister 114. A key difference, however, as shown best in FIG. 5A, is that the canister case 116 extends to about the top of the canister 114 so that the top of the canister case 116 is approximately flush with the top of the canister 114. A cutout 115 is in the side wall of the canister case which is slightly larger than an ordinary index finger and another similar cutout is in the opposite side wall. To activate the device to release medication, it is necessary to place one's index finger over this cutout while applying an axial force urging the canister 114 downward into the canister case 116, so that the finger can move downward into the cutout 115 as the canister 114 moves downward. If one applies an axial force with one's finger positioned other than over the cutout 115, the upper edge of the canister case 116 will take the force, and the canister 114 will not properly descend into the canister case 116 to activate the internal valve to release a jet of the medication or to actuate the mechanism to advance the indicator wheel.

The driver 170 includes a skirt 172. Spaced around the inside surface of the skirt 172 is a set of several bumps 175a having a thickness such that the skirt 172 can be snugly press-fitted over the canister 114 to hold the driver 170 onto the canister 114. It should be appreciated that the driver 170 could be replaced with the adhesive mount described in connection with FIG. 1 or some other mount and, likewise, the adhesive mount of FIG. 1 could be replaced with the press-fitted mount of FIG. 5.

Like the driver 70 of FIG. 1, the driver 170 of FIG. 5 includes an annular ring 175 above the base 172, with a set of upwardly protruding lugs 176. Each lug has a flexible lug body 177 and a lug point 178. Also on the annular ring 175 is a set of curved, flexible, upwardly extending pawls 180, all of which are essentially the same as in the embodiment of FIG. 1.

The indicator wheel 150 of the embodiment of FIG. 5 is essentially the same as the indicator wheel 50 of the embodiment of FIG. 1. It includes a top surface 152, a lower surface, a hole 156 through the middle, a set of upper surface teeth 158, and a set of lower surface teeth 160.

The outer cover 120 of the embodiment of FIG. 5 is somewhat similar to the outer cover 20 of the embodiment of FIG. 1, in that there is a roughly circular top 122, with a window 126 therethrough, an axially depending skirt 124 and a set of notches 129 spaced around the interior surface of the skirt 124. The axially depending skirt 124 differs from the axially depending skirt 24 of FIG. 1 in that the axially depending skirt 124 of the present embodiment is longer and includes a set of child resistant lugs 121 spaced around the radially inner surface thereof with the functions described below.

Figure 5B:
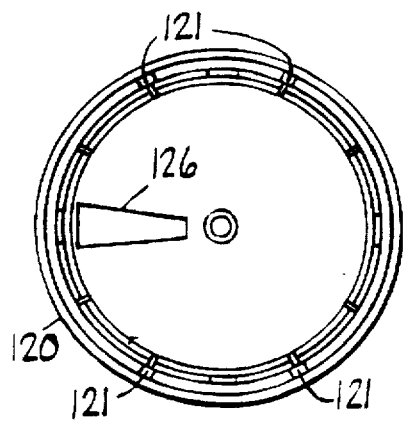
FIG. 5B is a bottom view of the outer cover of the invention.
Figure 5A:
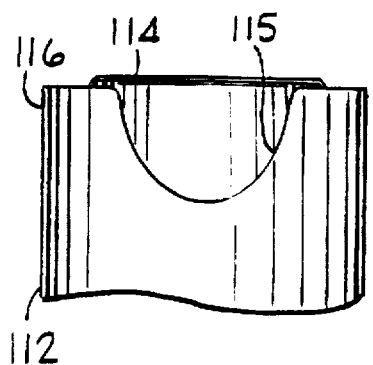
FIG. 5A is a side elevational view of a portion of canister and canister case used with an alternate embodiment of the invention.
Figure 5:
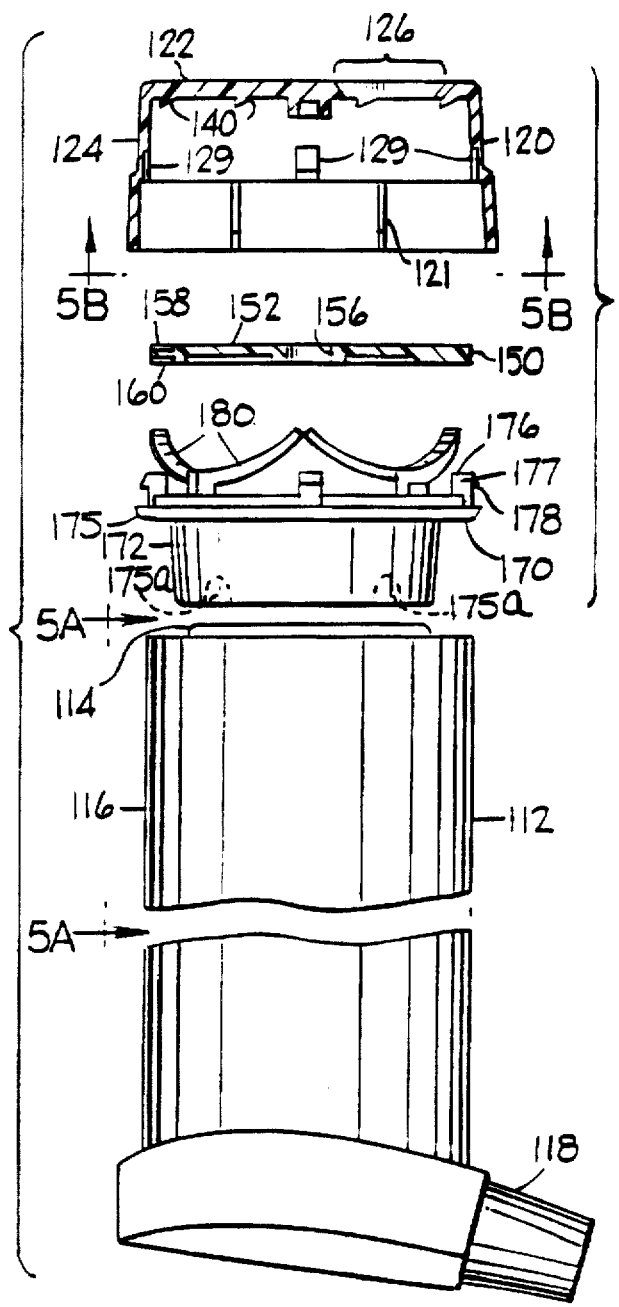
FIG. 5 is an exploded elevational view of an alternate embodiment of the present invention with a canister and canister case.

The child resistant lugs 121 are better shown in FIG. 5B, taken along line 5B—5B of FIG. 5. As can be appreciated from FIG. 5B, the child resistant lugs are not spaced equally, but instead there is a pair on one side and another pair on the opposite side. The two pairs of child resistant lugs 121 are spaced such that one pair can descend into the cutout 115 in the sidewall of the canister case 116 when the canister is depressed if that pair is centered over the cutout 115. At the same time, of course, the other pair descends into the cutout in the opposite sidewall. However, if the two pairs of child resistant lugs 121 are not centered over the cutouts, then the canister cannot be depressed to activate the valve in the canister case to release a jet of medication, because the child resistant lugs 121 will abut against the top of the canister case 116. Thus, to render the system child resistant, the device is rotated along with the attached canister 114 a non-integral multiple of 180° after it is used so that the two pairs of child resistant lugs 121 are not aligned over the cutouts 115. The next time it is used, the device along with the attached canister 114 must be rotated to realign the pairs of child resistant lugs over the two cutouts 115. Only then can the device descend over the canister case 116 while the child resistant lugs 121 descend into the cutouts 115. To tell the user when the pairs of child resistant lugs 121 are properly aligned over the cutouts 115 so that medication can be dispensed, there may be aligning arrows or other indicia (not shown) on the device and the canister case 116.

Figure 6:
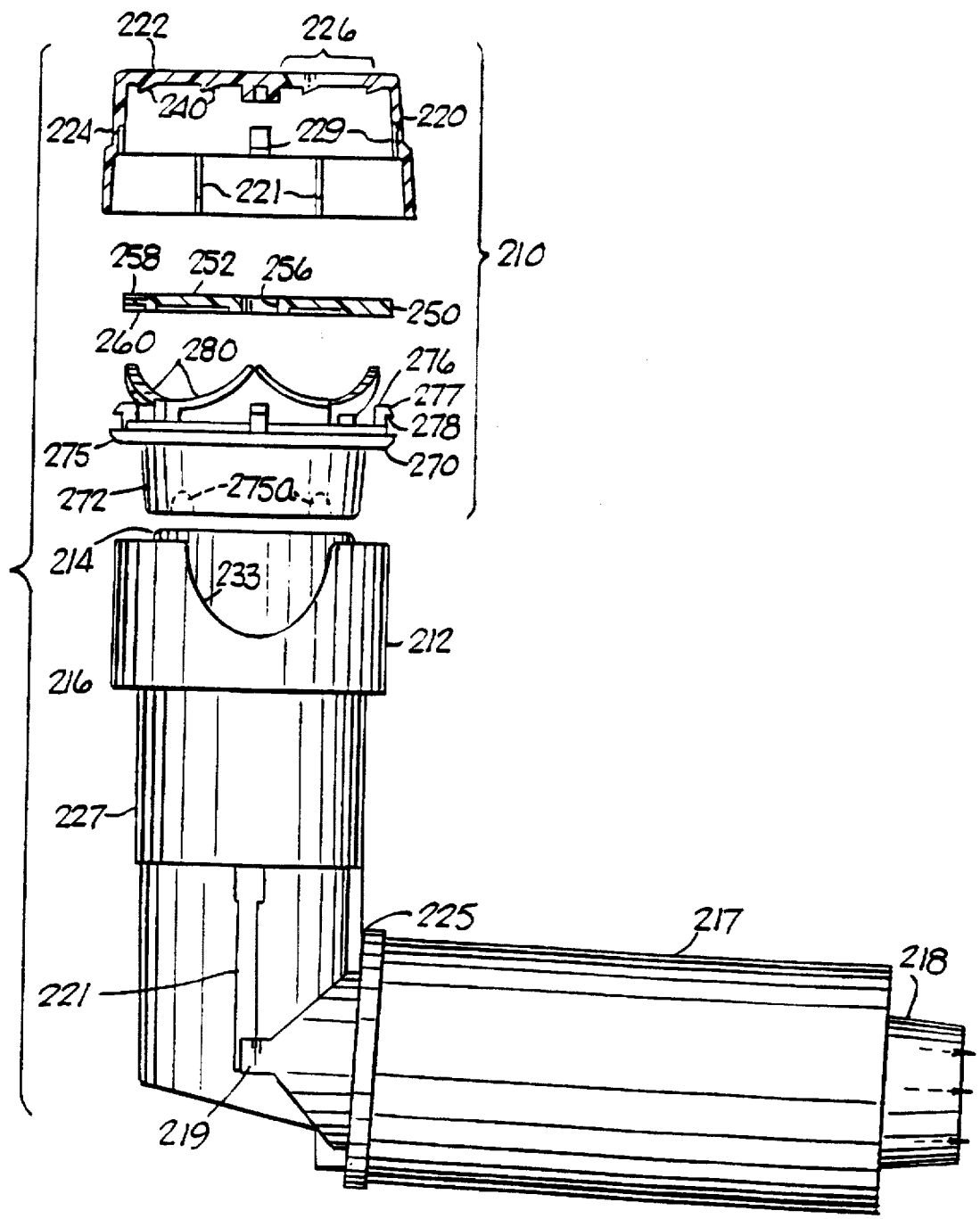
FIG. 6 is an exploded elevational view of an alternate embodiment of the present invention with a canister and canister case.

Next described is yet another alternative embodiment for use with still another aerosol medication canister case. FIG. 6 shows the dispenser 212 with a canister case 216, a driver 270, an indicator wheel 250 and an outer cover 220. The canister case 216 is a well known design in the art that is quite different from the canister cases 16 of FIG. 1 and 116 of FIG. 5 previously described. The canister case 216 includes a canister holder 227 and an aerosol chamber 217 with a dispensing mouth 218. The aerosol chamber 217 is a hollow cylinder which receives the canister holder 227 so that the entire canister case 216 collapses neatly into a package roughly the size of the aerosol chamber 217 when not in use. The canister case 216 includes a slot 221 in its lower portion which receives a tab 219 in the aerosol chamber 217. The canister case 216 also includes a longitudinal rib which engages a notch 225 in the aerosol chamber 217 when the device is readied for use as explained below.

To use the device, the canister holder 227 is telescoped out of the aerosol chamber 217. The canister holder 227 and aerosol chamber 217 are hinged to a right angle as shown in FIG. 6 by rotating the aerosol chamber tab 219 in the canister holder slot 221, and the right angle arrangement is secured by allowing the canister holder rib to engage the aerosol chamber notch 225. As mentioned above, the canister case 216 of the type shown in FIG. 6 is well known in the art and is in common use, and therefore it is not described in any additional detail here.

The invention 210 of FIG. 6 is to some extent essentially identical to the invention 110 of FIG. 5, in including a driver 270, an indicator wheel 250 and an outer cover 220, each of the same design as the driver 170, indicator wheel 150 and outer cover 120 of FIG. 5. (For ease of reference, the 200-series labels of FIG. 6 generally correspond to the 100-series labels of FIG. 5, wherein the last two digits are the same and the first digit is a "1" in FIG. 5 and a "2" in FIG. 6.)

The invention 210 is attached to the canister 214 by press-fitting the driver 270 onto the end of the canister 214 in the same manner as in the embodiment of FIG. 5. As can be seen in FIG. 6, the canister holder 216 includes a cutout 233 on one side and another cutout (not shown) on the opposite side. Like the cutout 115 of FIG. 5, the cutout 233 of FIG. 6 is designed to accommodate the user's finger when the canister 214 is depressed into the canister holder 227 to activate the internal valve to release a jet of medication. In the inventions of FIG. 5 and FIG. 6, however, that cutout is used to render the device child resistant. A set of two pairs of lugs 221 are on the interior surface of the skirt 224 of the outer cover 220. If each pair of lugs 221 is centered over a cutout 233, then the interior valve may be actuated to release medication by depressing the invention 210 downward toward the canister holder 227 so that the outer cover skirt 224 passes over the top of the canister holder 227 as each pair of lugs 221 descends into a cutout 233. However, if each pair of lugs 221 is not so centered over a cutout 233, then any attempt to actuate the internal valve to release a jet of medication, or to advance the indicator wheel by actuating the indicator mechanism, will be blocked by the lugs 221 abutting against the top of the canister holder 227. Thus, the device is rendered child resistant because the user must be certain that there is proper alignment between the invention 210 and the canister holder 216 (such as by lining up alignment marks that are not shown). This is an action that cannot normally be accomplished by young children.

Another means for making the device child-resistant involves the length of the depending skirt 224 of the outer cover 220. As explained above, the canister holder 227 telescopes out of the aerosol chamber 217 and then hinges to a roughly right angle to dispense medication. After the medication is dispensed, the canister holder 227 is collapsed back into the aerosol chamber 217. However, even in the collapsed state, medication can be dispensed by the user or by a child if the dispenser does not include the indicator device of the present invention, by simply pressing the end of the canister 214. This can be prevented by using the indicator device of the present invention and lengthening the depending skirt 224 to such an extent that it abuts against the end of the aerosol chamber 217 when the canister holder 227 is collapsed into the aerosol chamber 217, so that any force applied to the outer cover 220 is resisted by the aerosol chamber 217 and not transferred to the canister 214 to dispense medication. When the device is readied for use, the canister holder 227 is telescoped out of the aerosol chamber 217 and hinged to a right angle thereto, so that the outer cover skirt 224 no longer abuts against the end of the aerosol chamber 217, to allow a force applied to the outer cover 220 to be transferred to the canister 214 to actuate the internal valve and release the medication.

Another variation of the child-resistant aspect combines the elements explained above. An extended skirt 224 is utilized which prevents medication from being dispensed when the canister holder 227 is in its collapsed state, because the extended depending skirt abuts against the end of the aerosol chamber 217. When the device is readied for use, the canister holder 227 is telescoped out of the aerosol chamber 217 and hinged to a right angle thereto so that the outer cover skirt 224 no longer abuts against the end of the aerosol chamber 217, and the force applied to the top of the outer cover 229 can be transferred to the canister 214 to actuate the internal valve and release the medication. However, the device also includes in combination the two pairs of lugs 221 on the interior surface of the skirt 224 of the outer cover 220. As described above, these pairs of lugs 221 must be centered over the cutouts 233 in order to depress the device to release medication. Thus the device is rendered doubly child-resistant. The embodiment shown in FIG. 6 may also include a window on the skirt 224 of the outer cover 220 through which an arrow on the canister holder 227 is visible to ensure proper alignment of the lugs 221 over the cutouts 233.

Another embodiment of the invention 10 is shown in FIG. 8, the exploded view of FIG. 9, and the details of FIGS. 10 and 11. This embodiment includes three main elements: an activation button 320, an indicator wheel 350, and a driver 370. The activation button 320 includes a top 322 and an axially depending skirt 324 extending downward from the top. Through the top 322 is a window 326 similar to the window 26 of the FIG. 1 embodiment.

Spaced around the radially outer surface of the depending skirt 324 are a set of lugs 329, which are better shown in the sectional view detail of FIG. 10. Each lug 329 includes an upper wall 330 and a bevelled portion 333 which extends from the upper wall 330 to the bottom of the depending skirt 324. The circumferential width of the lug 329 is just enough to fit into the notch 376 of the driver 370 described below without allowing any significant circumferential play between the lugs 329 and those notches 376. The lugs and notches of the preferred embodiment may be reversed or may be replaced with a slot and groove or a hole and post or any other arrangement allowing limited axial movement of the outer cover relative to the retainer.

In the center of the bottom surface of the top portion 322 of the activation button 320 is an axially extending hub 336 which mates with a central hole 356 of the indicator wheel 350 in the manner described below. Also on the bottom surface of the top portion 322, around the periphery which meets the depending skirt 324, are a set of activation button teeth 340 which engage the indicator wheel teeth 358 in the manner described below. The outer cover teeth 340 include a ramp on one side and a face on the other side, in the manner of those shown in FIG. 2B in connection with the embodiment of that figure. The teeth 340 engage the indicator wheel teeth 358 to produce a ratchet effect between the activation button 320 and the indicator wheel 350 in the manner described below. Alternatively, of course, the ramp and face arrangement may be on each tooth 358 of the indicator wheel 350 while the teeth 340 of the activation button 320 are simple knife edges. The important point is that the activation button teeth 340 and indicator wheel teeth 358 allow one way rotation of the indicator wheel 350 with respect to the activation button 320.

The indicator wheel 350 is a disk-shaped element having an upper surface 352, a lower surface 354 and a hole 356 in the middle. The diameter of the disk-shaped indicator wheel 350 is such that it nests into the activation button 320. The upper surface 352 includes a set of indicator wheel upper teeth 358 around the periphery of the upper surface 352 and the lower surface 354 includes a set of indicator wheel lower teeth 360 around the periphery of the lower surface 354. The bottom surface may include a central hub 357 to rotate in the driver hub 381 in the manner described below. The indicator wheel teeth 358 and 360 are essentially the same as the respective elements 58 and 60 shown in the elevation detail of FIG. 3A. On the upper surface 352 of the indicator wheel 350 is a line which extends spirally from near the center to near the radially inner edge of the upper teeth 358, in the manner shown for the analogous element 50 in FIG. 3.

The driver 370 includes a downwardly extending skirt 372 configured to mate with the canister of the canister aerosol medication dispenser in the manner shown for the embodiment of FIG. 1. The driver 370 is attached to the canister by press-fitting the downwardly extending skirt 372 onto the canister end. The diameter of the downwardly extending skirt 372 is preferably just larger than the diameter of the canister and still smaller than the opening to the canister case, so that the downwardly extending skirt 372 can be pushed into the canister case if necessary to actuate the canister valve. Other mounts are feasible such as a clamp or a buckle, or mounts that make the driver integral with the canister or mounts that make the device resistant to operation by a child. Several mounting variations are described herein.

Above the downwardly extending skirt 372 on the driver 370 is a base 375 attached to the downwardly extending skirt 372 by a set of radially extending webs 381 spaced around the downwardly extending skirt 372. The webs 381 define a set of spaces 383 therebetween. Extending upward from the base 375 is an annular ring 377 with a set of notches 376. As better shown in the elevational detail of FIG. 11, each notch 376 has a first flat 381 and a second flat 378 separated by a step 379. The notches 376 of the driver 370 and the lugs 329 of the activation button 320 are dimensioned such that there is some axial play between the driver 370 and the outer cover 320; that is, the lugs 329 may extend all the way into the notches 376 while the outer cover 320 and driver 370 are positioned closely together, or the lugs 329 may be partially withdrawn from the notches 376 while the outer cover 320 and driver 370 are positioned farther apart.

Also extending upward from the base 375 of the driver 370 is a set of driver pawls 380. Each driver pawl 380 includes a pawl base and a curved flexible pawl body which extends circumferentially or tangentially, and upwardly, to terminate in a pawl end, all essentially the same as in the pawl 80 of FIGS. 1 and 4B. The pawl end engages the indicator wheel lower teeth 360 in a ratcheting manner whereby the pawl end passes over the ramp portion of the indicator wheel lower teeth. An important aspect of this embodiment of the invention is that the flexing of the pawls 380 produces an elongation of the circumferential dimension of the pawl, as in the embodiment of FIG. 1.

The device is operated essentially the same as the embodiment of FIG. 1 but with certain advantages over that embodiment. An axial force is applied urging the actuation button 320 toward the canister. The application of such a force produces several kinds of movements, which may occur simultaneously with one another or in sequence in any order. One kind of movement is the actuation of the valve of the canister to release a measured amount of aerosol medication from the canister and out the outlet of the canister case. The other kind of movement produced by the application of an axial force urging the activation button 320 toward the canister is movement within the device 310. The axial force on the activation button 320 moves the activation button 320 toward the driver 370.

This second kind of movement—the moving together of the activation button 320 and driver 370 caused by the axial force applied to the activation button 320—also depresses the driver pawls 380, the ends of which are engaged by the indicator wheel lower teeth 360. This depression—or flexing—of the driver pawls, as explained above, results in a circumferential or tangential lengthening of the pawls due to the pivoting of the pawl body about the pawl base and the flexing along the pawl body. Because the pawl end is engaged with the indicator wheel lower teeth 360, this circumferential or tangential lengthening of the driver pawls 380 drives the indicator wheel through an incremental circumferential distance, thus producing a rotation of the indicator wheel 350 relative to the driver 370. The indicator wheel lower teeth 360 and driver pawls 380 are dimensioned such that this incremental circumferential or tangential shift is the length of a single tooth of the indicator wheel lower teeth 360. The rotation of the indicator wheel 350 does not translate into any rotation of the activation button 320, because the activation button 320 is rotationally fixed in relation to the driver 380 by the engagement of the activation button lugs 329 in the driver notches 376.

This counterclockwise rotation of the indicator wheel 350 in relation to the activation button 320 shifts to the window 326 of the activation button 320 a new portion of the indicator wheel upper surface 352. Because the upper surface 352 includes a spiral line or pattern as explained above which appears as a "gauge" when viewed through the window 326, the progressive rotational shift of the upper portion 352 viewable through the window has the effect of creating a declining or ascending line in the window. Thus, the repeated application of an axial force to the activation button 320 gradually rotates the indicator wheel 350 to result in the appearance of a declining or ascending "gauge" in the window 326.

The release of the axial force urging the activation button 320 toward the canister, allows the flexed driver pawls 380 to unflex toward their more natural relaxed position. This unflexing of the driver pawls 380 forces the activation button 320 and indicator wheel 350 away from the driver 380. The unflexing of the driver pawls 380 causes the pawl ends to shift back circumferentially or tangentially. However, this circumferential or tangential shifting of the pawl ends as the pawls 380 unflex does not produce any rotation of the indicator wheel 350. This is because the indicator wheel lower teeth 360 and pawl ends produce a one-way ratchet effect.

This rotation of the indicator wheel 350 in relation to both the activation button 320 and driver 380 has one other important effect. As the indicator wheel 350 rotates in relation to the activation button 320, the activation button teeth 340 ride over the indicator wheel upper teeth 358. The activation button teeth 340 and indicator wheel upper teeth 358 are dimensioned such that the circumferential shift of the pawl ends in the course of one cycle of applying an axial force urging the outer cover 320 toward the driver 380, causes the indicator wheel upper teeth 358 to shift one tooth in relation to the activation button teeth 340. When the outer cover teeth 340 drop over the face of the indicator wheel upper teeth 358 as this one-tooth shift occurs, an audible "click" results. This "click" confirms to the user that the indicator wheel has properly advanced.

The indicator wheel lower teeth 360, as mentioned above, are dimensioned such that the circumferential movement of the pawl ends produced by applying or releasing an axial force to the activation button 320, corresponds to one tooth. Therefore, the circumferential shift in the pawl ends resulting from releasing the axial force on the activation button 320, is equal to one tooth. The passing of the driver pawls 380 over a tooth of the indicator wheel lower teeth 360, produces another audible "click". This "click", unlike the first "click" previously described, does not confirm any advancement of the indicator wheel 350, since the indicator wheel 350 does not advance at that time; rather, this "click" confirms that the driver pawls 380 have advanced by one tooth in the indicator wheel lower teeth 360, so that the driver pawls 380 will advance the indicator wheel 350 the next time an axial force is applied to the flex the driver pawls 386.

When the axial force is released from the activation button 320 so that the driver pawls are permitted to unflex, the indicator wheel 350 is positively prevented from rotating back to its previous position before it was last advanced, by the engagement of the indicator wheel upper teeth 358 with the activation button teeth 340. As described above, those sets of teeth 358 and 340 act as a one-way ratchet; rotation of the indicator wheel 350 is allowed in one direction, but rotation of the indicator wheel 350 is prevented in the other direction, but rotation of the indicator wheel 350 is prevented in the other direction.

As in the embodiment of FIG. 1 and the other embodiments described herein, it will be apparent to those skilled in the art that some of these arrangements may be revised or reversed without departing from the scope or spirit of the invention. For example, without limitation, the teeth and pawls could be designed so that the indicator wheel advances when the force on the outer cover is released so that the outer cover and driver separate rather than when a force is applied so that the outer cover and driver come together; the pawls could be on the indicator wheel and the engaged teeth on the driver rather than the other way around; the outer cover teeth and indicator wheel upper teeth could be reversed; and the pawls could be between the outer cover and the indicator wheel rather than between the indicator wheel and driver so that the pawls are positioned on the indicator wheel upper surface or the outer cover lower surface. It will also be apparent that the pawls and teeth on the various elements could be positioned on the outer circumference extending radially outward (or the inner circumference extending radially inward in the case of a disk having a center hole), rather than on the upper or lower surfaces extending upward or downward.

Figure 12:
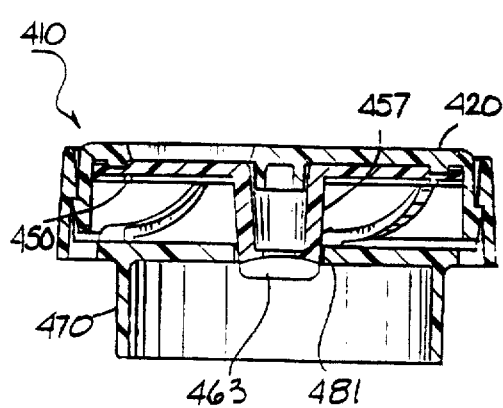
FIG. 12 is a side sectional view of an alternate embodiment of the present invention.
Figure 13:
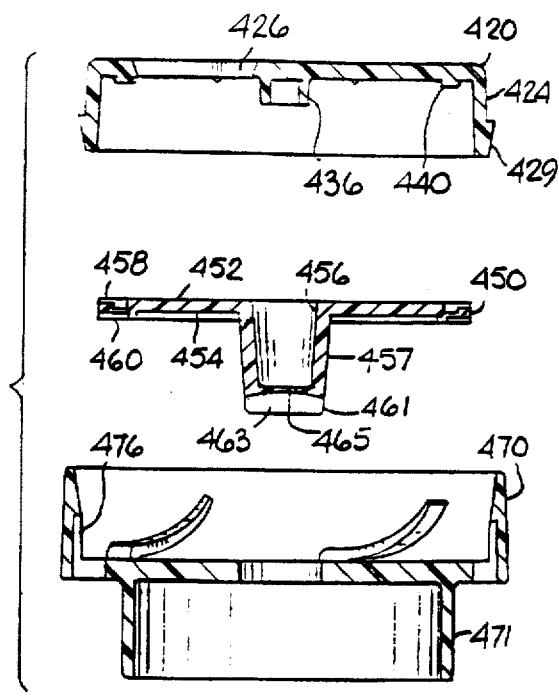
FIG. 13 is an exploded side sectional view of the alternate embodiment of FIG. 12.

Another preferred embodiment of the invention is shown in FIGS. 12–13, wherein FIG. 12 is a sectional view and FIG. 13 is an exploded sectional view. This embodiment is similar to the embodiments previously described, except that it includes the additional advantageous feature of a reset means to reset the indicator wheel to its starting position. There ere several circumstances in which such a reset means is desirable. The gauge defined by the indicia or the indicator wheel viewed through the outer cover window may extend less than 360° around the top surface of the indicator wheel. In that event, the gauge will read "empty" or the equivalent, and the medication in the canister will be exhausted, but the indicator wheel will not have rotated a complete revolution. This presents no problem if the device is used for only a single medication canister and then discarded. However, the device is easily capable of a durable design that can be used repeatedly with many canisters. If the device is reused in that manner, and the indicator wheel is not set back at the "start" position correctly after the "empty" position, because the "gauge" does not extend all the way around the indicator wheel, then it is necessary to reset the gauge by rotating the indicator wheel with respect to the outer cover. Such resetting may also be necessary, even if the gauge extends all the way around the indicator wheel, if the gauge extends a non-integral multiple of 360° around the indicator wheel.

The principal elements of this embodiment 410 as shown in FIGS. 12 and 13 are an activation button 420, an indicator wheel 450 and a driver 470. The activation button 420 is quite similar to the activation button 320 and the indicator wheel 450 is quite similar to the indicator wheel 350, described in connection with the previously-described embodiment of FIGS. 8 and 9. The activation button 420 includes a circular top 422 with a window 426 therethrough, and an axially depending skirt 424 having a set of tabs 429 spaced around the bottom thereof. A hub 436 extends downward from the bottom surface of the top 422. A set of outer cover teeth 440 extend around the periphery of the bottom surface of the top 422.

The indicator wheel 450 includes a top surface 452 with a set of teeth 458 extending around the periphery to engage the outer cover teeth 440, and a bottom surface 454 with a set of teeth 460 extending around the periphery to engage the pawls of the driver described below. The top surface 452 also includes a spiral line or other indicia viewable through the activation button window 426 in the same manner as the indicator wheels of the embodiments previously described. The indicator wheel 450 nests inside the activation button 420 in the manner shown in FIG. 12.

An important difference between the indicator wheel 450 of FIGS. 12 and 13 and the indicator wheels of the embodiments previously described, is the axially extending hub 457 of the indicator wheel 450 of FIGS. 12 and 13. The axially extending hub 457 includes a central hole 556 extending through the top surface 452 of the indicator wheel 457. The central hole 556 receives the hub 436 of the activation button 420 to help maintain the indicator wheel 450 in nesting relationship with the actuation button 420. The axially extending hub 457 is defined by an annular wall extending in the axially downward direction from the bottom surface of the indicator wheel 450. At the bottom end of the axially extending hub 457 is a reset button 461 having a transverse slot 463 therein. The base of the reset button slot 463 may optionally include a hole 465 extending from the reset button slot 463 through to the central hole 456 to assist in molding the piece. The axially extending hub 457 is received by the driver 470 in the manner described below.

The driver 470 is similar in design and operation to the driver 370 described in connection with the embodiment of FIGS. 9–11. It includes a skirt 471 that can be press-fitted onto the end of a canister, a set of pawls 480 to engage the teeth 460 on the lower side of the indicator wheel 450, and a set of notches 476 to receive the tabs 429 of the activation button.

Importantly, the driver 470 of the embodiment of FIGS. 12–13 has a hub-receiving hole 481 which receives the axially extending hub 457 of the indicator wheel 450 in the manner shown in FIG. 12. As that figure indicates, the axially extending hub 457 protrudes part way through the hub-receiving hole 481 so that the slot 463 in the end of the hub can be accessed from beneath the driver 470.

The device 410 of FIGS. 12–13 is operated much like the devices of the embodiments previously described. The assembled device as shown in FIG. 12 is attached permanently or temporarily to a canister by press fitting the skirt 471 of the driver 470 over the canister end. Other attachment systems including those alternatives described herein may be used in place of or in addition to the press fit arrangement. Medication is dispensed, and the indicia on the indicator wheel 450 is advanced past the window 426 of the actuation button 420, by applying a force in the axial direction to the top of the activation button 420.

The operation of the indicator mechanism has been described in some detail in connection with the embodiments described above, and thus detailed description is not repeated here. Briefly, the axial force depresses the activation button 420 and indicator wheel 450 in relation to the driver 470 by allowing the tabs 429 of the activation button 420 to slide farther into the notches 476 of the driver 470. This depression is yieldingly resisted by the spring force of the pawls 480 of the driver 470 which are engaged with the teeth 460 on the lower surface of the indicator wheel 450. The pawls 480 flex downward to accommodate the depression of the indicator wheel 450 toward the driver 480. In so flexing, the tips of the pawls 480 move circumferentially if the pawls 480 are curved around the perimeter of the indicator wheel 450, or move tangentially if the pawls 480 are tangential with respect to the perimeter of the indicator wheel 450. This circumferential or tangential movement of the tips of the pawls 480 drives the indicator wheel 450 to rotate in relation to the driver 470 and the activation button 420 which is rotatively fixed in relation to the driver 470 by the engagement of the activation button tabs 429 with the driver notches 476, because the tips of the pawls 480 are engaged with the teeth 460 on the lower surface of the indicator wheel 450 in a one-way ratchet arrangement.

As the indicator wheel 450 rotates in relation to the activation button 420, the teeth 458 on the upper surface of the indicator wheel 450 slide past the engaged teeth 440 on the lower surface of the activation button 420. These two sets of teeth are also in a one-way ratchet arrangement, but in a direction opposite the one-way ratchet arrangement of the teeth 460 on the bottom surface of the indicator wheel 450 and the pawls 480 of the driver 470. Therefore, the teeth 458 on the upper surface of the indicator wheel 450 can pass over the teeth 440 on the lower surface of the activation button 420. As they do so, a "click" or set of "clicks" is audible.

The application of an axial force to the top of the activation button 420 also depresses the canister in the canister case, resulting in the activation of the canister valve to release medication. Thus, the single application of axial force to the activation button 420 results in the release of a measured dose of medication for the user and advances the indicia of the indicator wheel 450 past the window 426 of the activation button 420 to record such release of medication.

When the axial force is discontinued from the top of the activation button 420, the spring force of the pawls 480 (or from a separate spring, or from both) raise the indicator wheel 450 and activation button 420 in relation to driver 470. The relaxing of the pawls 480 results in the tips of the pawls 480 raising and moving in a circumferential or tangential direction opposite the circumferential or tangential direction in which they moved when the activation button 420 and indicator wheel 450 were depressed. The one-way ratchet arrangement between the teeth 460 on the lower surface of the indicator wheel 450 and the pawls 480 allow the pawls 480 to pass over those teeth 460. Therefore, the pawls 480 do not drive the indicator wheel 450 to rotate in relation to the activation button 420 and driver 470 upon the release of the axial force. This passing of the pawls 480 over the teeth 460 on the lower surface of the indicator wheel 450 produces another "click" or set of "clicks" to confirm the proper operation of the device.

An important difference in the operation of the embodiment shown in FIGS. 12–13 and the operation of the embodiments previously described, involves the use of the reset button 457. The user may reset the indicator wheel to indicate that no medication has been released from a particular canister. This is most likely to occur when the user desires to re-use the device with a new canister after exhausting the medication in an old canister, but may occur under other circumstances as well, such as to correct mistaken operation of the device. The reset is achieved by removing the device 410 from the canister so that the underside of the driver 470 can be accessed. The reset button 457 is then turned by sliding a coin, a fingernail, a screwdriver or any other suitable flat surface into the slot 463 of the reset button 457. The rotation of the reset button 457 rotates the entire indicator wheel 450, and the rotation is continued until the desired indicia on the indicator wheel 450 are observed through the window 426 of the activation button 420. The reset button 457 can be rotated in only one direction, since the indicator wheel 450 can be rotated in only one direction due to the one-way rachet arrangement between the teeth 458 on the upper side of the indicator wheel 450 and the teeth 440 on the activation button 420.

Figure 14:
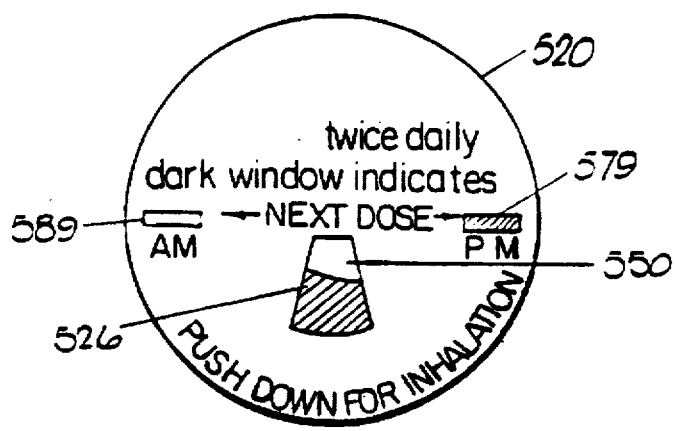
FIG. 14 is a top view of an alternate embodiment of the present invention.
Figure 15:
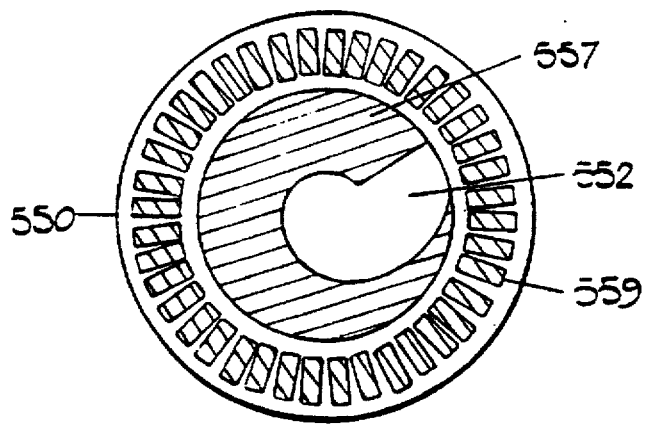
FIG. 15 is a top view of the indicator wheel of the embodiment of FIG. 13.

Another variation of the invention is shown in FIGS. 14 and 15, which is useful to remind a user to take medication, as well as to show how much medication remains. As in the other embodiments, the device 510 of FIG. 14 includes an activation button 520, an indicator wheel 550, and a driver (not shown, but the same as the other embodiments, such as shown in FIGS. 12–13). The indicator wheel 550 is essentially the same as the indicator wheels of the other embodiments, and includes a spiral line dividing one color 567 from another color 552. The spiral is visible through a window 526 in the outer cover 520. As in the other embodiments described herein, the application of an axial force to the activation button 520 dispenses a measured dose of medication from the canister valve, and also rotates the indicator wheel 550 in relation to the activation button 520. The rotation of the indicator wheel 550 in relation to the activation button 420 advances the spiral line dividing the two colors 557 and 552 on the indicator wheel 550 past the window 526 of the activation button 520, to produce the effect of a declining or advancing "gauge." By calibrating the configuration of the spiral line—and thus the gauge—to the amount of medication in the container and the amount released by a single dose, the device functions to show the gradual consumption of medication from a full canister to an empty canister. Several elements are omitted for clarity in FIGS. 14–15, such as the teeth on the upper surface of the indicator wheel 550.

An important difference between the embodiment of FIGS. 14–15 and the embodiments previously described involves a system to remind the user to dispense medication at set intervals. The activation button 520 includes a pair of reminder windows 589 and 579 extending through the top thereof. The indicator wheel 550 includes a set of colored elements 559 extending around the periphery thereof, positioned to be selectively viewable through the windows 579 and 589 of the activation button 520.

The spacing and positioning of the colored elements 559 in relation to the spacing and positioning of the windows 579 and 589, are such that a colored element is viewable through one window 579 or the other window 589 but not through both windows simultaneously. Thus, by labelling the windows 579 and 589, the device can indicate the date or time of time for the next required dose of medication. In the embodiment of FIGS. 14–15, the windows 579 and 589 are labelled "AM" and "PM" as abbreviations for morning and afternoon. The colored elements 559 are spaced around the periphery of the indicator wheel 550 to require two administration of medication for the indicator wheel 550 to rotate from a given colored element 559 to the next colored element 559. The circumferential spacing between the windows 579 and 589 is such that if a colored element 559 is visible through one window 579 then no colored element 559 will be visible through the other window 589, and if a colored element 559 is visible through the other window 589 then no colored element 559 will be visible through the first window 579.

In operation, the device is used to remind users to administer medication once in the morning and once in the afternoon. The device will start with a colored element 559 showing through the "AM" window 589 and no colored element showing through the "PM" window 589. When medication is administered by applying an axial force to the activation button 520 to release medication from the actuation valve of the canister, the activation button 520 and indicator wheel 550 depress in relation to the driver. This depression causes the pawls of the driver to drive the teeth on the bottom surface of the indicator wheel 550 to rotate the indicator wheel 550 in relation to both the driver and the activation button 520. The dimensions and configuration of the various elements are such that the amount of rotation of the indicator wheel 550 displaces the colored element 559 from the "AM" window 589 so that no colored element 559 shows through that window 589. The rotation also shifts a colored element 559 into view through the "PM" window 579, where previously no colored element 559 was visible. Thus, the device now shows a colored element in the "PM" window 579 but not the "AM" window 589, thereby indicating that the next dose is to be administered in the afternoon. The indicator wheel 550 rotates another increment the next time medication is administered, in the afternoon, so that a colored element 559 once again is visible on the "AM" window 589 but not the "PM" window 579. The user is thus reminded that the next dose is to be administered in the morning.

Figure 18:
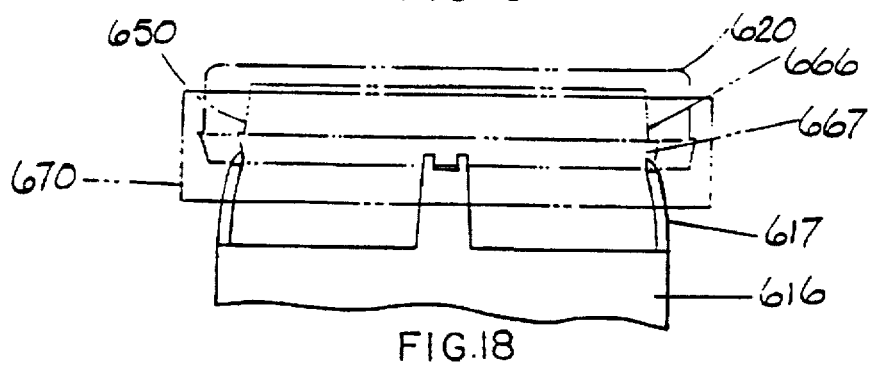
FIG. 18 is a side sectional view of the embodiment of FIG. 16.
Figure 17:
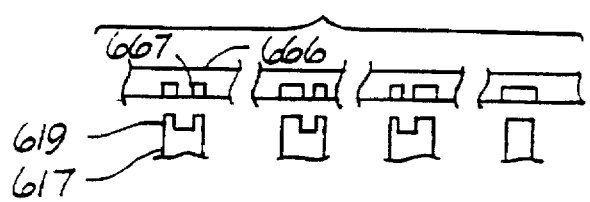
FIG. 17 is a diagrammatic elevation view of a detail of the embodiment of FIG. 16.

Other variations of the window reminder system described in the immediately preceding paragraphs are possible. The windows could be three or more in number, with appropriate modification to the spacing of the colored elements, to remind the user to take medication three times a day such as morning, afternoon and evening. The device could be used to remind the user of the next day that the medication is to be administered, rather than the next time of day, by replacing the "AM" and "PM" labels with day abbreviations such as "SUN""TUE" and so Another embodiment of the invention is shown in FIGS. 16–18 which is useful for ensuring that the user does not inadvertently or deliberately continue attempting to dispense medication from the canister after the medication is substantially exhausted. The device 610 of this embodiment includes an indicator mechanism comprising an activation button 620, and indicator wheel 650 and a driver 670, and a canister case 616 for holding a medication aerosol canister 614. The indicator mechanism components are similar to those described in connection with the embodiments previously identified. The activation button 620 includes a top 622 with a window 626 therethrough and a depending skirt 624 with a set of lugs 629 spaced around the bottom periphery. A set of teeth 640 are positioned on the lower surface of the top 622 to engage the indicator wheel teeth described below. A hub 636 is also positioned on the lower surface of the top 622.

The indicator wheel 650 includes an upper surface 652 having a set of teeth 658 around the periphery thereof to engage the teeth 640 of the actuator button 620 and includes a lower surface having a set of teeth 660 to engage the teeth of the driver described below. Through the center of the indicator wheel 650 is a hole 656 to receive the hub 636 of the activation button 620 to assist in maintaining axial alignment between the activation button 620 and indicator wheel 650. The lower surface of the indicator wheel 650 includes an axially extending indicator wheel hub 657 to engage the driver 670 in the manner described below.

Unlike the indicator wheels generally used in the embodiments previously described, the indicator wheel 650 of the embodiment of FIGS. 16–18 includes depending skirt 666 which has a set of keyholed flanges 667 spaced around the bottom periphery as better shown in the detail of FIG. 18. The keyholed flanges 667 (four in the embodiment shown, but there could be more or less as explained below) are thickened portions on the bottom periphery of the depending skirt 666. Each thickened portion has a unique notch or "keyhole" which receives the canister case keys in the manner described below.

The driver 670 includes a set of upwardly and circumferentially or tangentially extending pawls 680 mounted on an annular portion. An upwardly extending portion 675 includes a set of notches 676 to receive the tabs 629 of the actuator button 620 in a manner to prevent rotative movement but allow limited axial movement between the activation button 620 and driver 670, as previously described in connection with the other embodiments of the invention. A center portion 691 receives the hub 657 of the indicator wheel 650. The bottom of the center portion 691 is adapted to be glued or otherwise adhered to the end of the canister, although other attachment means are equally feasible including the alternative means described herein. A set of tab holes 671 are in the driver 670 to receive the tabs 617 in the manner described below.

The canister case 616 includes a set of key tabs 617 extending upwardly from the upper edge of the canister case 616. The tabs 617 extend upward and through the tab holes 671 in the driver 670 to engage the indicator wheel 650. The number of such tabs 617 preferably is the same as the number of keyed flanges 667 on the indicator wheel 650, as will be apparent from the discussion below. The key tabs 617 may be integral with the canister case 616, or may be attached to another element that is separately attached to the canister case 616, such as the tab mount 618 shown in FIG. 16.

The upper tip of each tab 617 terminates in a unique key 619 as better shown in the detail of FIG. 18. The aspect of the keys 619 and keyholes 667 is to establish a one-to-one match. That match may be achieved in a variety of ways; in the preferred embodiment, it is by defining unique notches that constitute keyholes 667 and unique tabs that constitute keys 619 that fit into the keyholes. Each keyhole 667 will accept only one of the keys 619, and each key 619 will fit into only one of the keyholes 667.

As best shown in the view of FIG. 18, the keyholed flanges 667 bias the keyed tabs 617 radially outward, or in other words spread the tabs 617 apart slightly. Therefore, the tabs 617 are continually urged radially inward toward the indicator wheel 650. As the indicator wheel 650 rotates in relation to the driver 670, and hence the tabs 617, the radially outer surface of the depending skirt 666 slides past the tabs 617 being urged against the skirt 666, overcoming the slight frictional resistance produced by the stationary tabs 617 on the moving skirting 666. When the indicator wheel 650 rotates to a position wherein all the keys 619 align with the keyholes of the keyholed flange 667, the keys 619 are snapped into the keyholes by the biasing force of the tabs 617. At that point, the indicator wheel 650 becomes rotatively locked in relation to the tabs 617 and the rest of the device. Moreover, as explained in more detail below in connection with the description of the operation of the device, the locking of the keys into the keyholes effectively disables the medication device by preventing the application of a force to the top of the activation button 620 from depressing the canister 614 into the canister case 616 to actuate the canister valve to release medication.

In operation, the user periodically dispenses medication in the manner described for the other embodiments set forth herein, that is by applying an axial force to the top 62 of the activation button 620. The axial force is transferred through the indication mechanism, comprising the activation button 620, indicator wheel 650 and driver 670, and onto the canister 614 to depress the canister into the canister case 616. Such depression actuates the canister valve at the bottom of the canister 614 to release a measured dose of medication into the canister case 616 for inhalation by the patient. The axial force applied to the top 622 of the activation button 620 also depresses the activation button 620 and indicator wheel 650 in relation to the driver 670, by biasing the pawls 680 downward. Such biasing advances the indicator wheel 650 due to the engagement of the pawls 680 with the indicator wheel lower teeth 660. The successive application of this axial force through multiple doses of medication gradually advances the indicator wheel in relation to the rest of the indicator mechanism, including the activation button 620 to produce a gradual change on indicia visible on the indicator wheel through the activation button window 626. Upon the release of the axial force from the top 622 of the activation button 620, the canister valve springs back to its relaxed state, thereby raising the canister 614 in relation to the canister case 616. Also, the pawls 680 bias back upward to raise the activation button 620 and indicator wheel 650 in relation to the driver 670. This raising motion results in the curved pawls 680 snapping over the lower teeth 660 of the indicator wheel 660. All of this portion of the operation is similar to the operation of the other embodiments described herein, and reference is made to that portion of the descriptions above.

The aspect of the present embodiment that is different from the other embodiments described above involves the locking action produced by the keyed tabs 617 in the keyholed flanges 667. As explained above, the keyed tabs 617 are biased outwardly by the indicator wheel 650. As the indicator wheel 650 rotates, the skirt 666 slides past the biased tabs 617. In addition, each time an axial force is applied to the top 622 of the activation button 620 to depress the activation button 620 and indicator wheel 650 in relation to the driver 670 and canister case 616, the indicator wheel 650 also shifts downward in relation to the tabs 617. This downward shift is readily accommodated by the configuration of the device; the tabs 617 simple ride upward as the radially outward face of the skirt 666.

When the indicator wheel 650 has rotated sufficiently through multiple medication dosing that the keys 619 align with the keyholes as shown in FIG. 18, the biasing force of the tabs 617 causes the tabs 617 to snap radially inwardly so that the keys fit into the keyholes. At that position, there are two effects: first, the indicator wheel can no longer rotate to advance the indicator wheel indicia, and, second, the canister 614 cannot be depressed in relation to the canister case 616 to dispense medication. That is because any axial force applied to the top 622 of the activation button 620 is simply transferred through the indicator wheel 650 and into the tabs 617, without producing any depression of the canister 614 in relation to the canister case 616 or any depression of the activation button 620 and indicator wheel 650 in relation to the driver 670.

In the embodiment depicted, there are four tabs 617. It can be appreciated that a single tab 617 would be sufficient to accomplish the purpose described above. In that case, there would be no need to configure special key and keyhole configuration; a simple tab and notch would suffice. However, it has been found desirable to use a plurality of tabs 617 so that the axial force applied to the top 622 of the activation button 620 is transferred to the canister 616 substantially equally around the circumference of the device in order to prevent binding, bending or breaking. The use of multiple tabs 617 is what necessitates unique and differing key and keyhole arrangements. If all the keys were the same, and all the keyholes were the same, then the device would lockup through a partial revolution of the indicator wheel 650, rather than upon a complete revolution. Thus, a substantial portion of the indicia-carrying capacity would be lost. For example, if all the keys were the same and all the keyholes were the same, and four equally spaced tabs 617 were used, then the device would lockup when the indicator wheel 650 had rotated only one-quarter revolution or less. Thus, at least three-quarters of the indicia-carrying capacity of the indicator wheel 650 would be left unused.

This obstacle is overcome by using different keys and keyholes for each pair of four matching keys and keyholes, as shown schematically in FIG. 18. When the set keys rotate sufficiently to align with the first set of keyholes, the keys do not match the keyholes. Therefore, the keys do not pass into the keyholes to lockup the device, but instead simply pass over those keyholes. The same occurs at the second set of keyholes and third set of keyholes. Finally at the fourth set of keyholes the keys match the keyholes, and so the set of four keys passes into the keyholes to lockup the device. In this manner, the indicator wheel must make substantially one entire revolution before the device locks up, thereby ensuring substantially complete use of the indicia-carrying capacity of the indicator wheel 650.

What is claimed:

1. A device to administer aerosol medication to a patient, comprising:
    (a) a dispenser including a canister with an interior holding pressurized aerosol medication, the canister having a first end with an outlet port and a second end, the outlet port being separated from the canister interior by an actuation valve that is actuable to establish communication between the outlet port and the canister interior, and a second end opposite the first end; and a canister holder holding the canister, the canister holder being in communication with the canister port whereby the displacement of the canister in relation to the canister port whereby actuates the actuation valve to release medication from the canister to an interior of the canister holder, and the canister holder having a canister holder outlet in communication with the canister holder interior to allow medication to flow from the canister interior through the canister outlet to the patient; and
    (b) an indicator mechanism attached to the dispenser above the canister adjacent the second end, the indicator mechanism including an indicator rotatable about and moveable parallel to an axis of rotation upon the displacement of said canister in relation to the canister holder; and a rotation mechanism for rotating said indicator upon movement of said indicator mechanism parallel to said axis of rotation; said indicator being rotated in the plane perpendicular to said axis of rotation; and a set of indicia to indicate rotation of the indicator.

2. The device of claim 1, wherein said indicator mechanism further includes an actuator to receive a force to displace the canister in relation to the canister holder and to rotate the indicator.

3. The device of claim 2, wherein said rotation mechanism includes at least one pawl and a set of pawl engaging-teeth, whereby the movement of the indicator mechanism parallel to said axis of rotation flexes the pawl to drive the teeth to produce rotation of the indicator in relation to the actuator.

4. The device of claim 3, wherein said pawl is on at least one of the actuator and the indicator and extends therebetween and said pawl-engaging teeth is on at least the other of the actuator and the indicator.

5. The device of claim 4, wherein said pawl is curved.

6. The device of claim 4, wherein said pawl includes a dimension substantially parallel to a plane containing said pawl-engaging teeth and wherein said pawl is configured such that said dimension lengthens as the pawl flexes against said pawl-engaging teeth.

7. The device of claim 4, wherein said pawl includes a substantially flat surface and the pawl-engaging teeth include substantially flat surfaces engageable with the substantially flat surface of the pawl.

8. The device of claim 4, wherein said pawl biases the pawl-engaging teeth from the pawl.

9. The device of claim 4, wherein said actuator includes a first actuator member and a second actuator member moveable parallel to said axis of rotation in relation to the first actuator member.

10. The device of claim 9, wherein the first actuator member and the second actuator member are joined by a notch on one of the first actuator member and second actuator member and a lug or the other of the first actuator member and second actuator member, the lug being limitedly moveable substantially parallel to said axis of rotation in relation to the notch to allow limited movement of the first actuator member parallel to said axis of rotation in relation to the second actuator member.

11. The device of claim 10, wherein said lug and said notch are configured to substantially prevent rotation of the second actuator member in relation to the first actuator member.

12. The device of claim 11, wherein said lug and said notch attach the second actuator member to the first actuator member.

13. The device of claim 4, wherein at least one of the first actuator member and the second actuator member includes a mount for mounting to the dispenser.

14. The device of claim 13, wherein said mount includes a cavity positionable on said canister second end.

15. The device of claim 14, wherein said cavity is sized so as to allow the actuator to be press-fit onto the canister.

16. The device of claim 13, wherein the mount is adapted to be adhered to the dispenser.

17. The device of claim 16, wherein the mount is adapted to be adhered to said canister second end.

18. The device of claim 4, wherein one of the dispenser and the indicator mechanism includes an interfering member and the other of the dispenser and the indicator mechanism includes a mating interfering member to interfere with the canister from being displaced in relation to the canister holder when the indicator rotates to a predetermined position.

19. The device of claim 18, wherein the interfering member includes a tab on one of the dispenser and indicator mechanism and extending toward the other of the dispenser and indicator mechanism and the mating interfering member includes a tab lock on the other of the dispenser and indicator mechanism whereby the rotation of the indicator to the predetermined position locks the tab with the tab lock.

20. The device of claim 18 wherein the interfering member includes a tab extending from the canister holder toward the indicator, and wherein the mating interfering member is adjacent an opening in the indicator, whereby the tab is received by the opening upon displacement of the canister in relation to the canister holder when the indicator is not rotated to said predetermined position, but the tab is stopped by the interfering member to prevent the displacement of the canister in relation to the canister holder when the indicator is rotated to said predetermined position.

21. A method for administering to a patient an aerosol medication contained in a canister having a pressurized interior containing medication, an outlet port at a first end an actuation valve separating the interior from the port and a second end, the method comprising:

(a) installing the canister into a canister holder, the canister and canister holder thereby constituting a dispenser, the canister being installed in the canister holder in a manner to allow the actuation of the actuation valve to release medication from the canister by applying an actuation force to the canister to displace the canister in relation to the canister holder;

(b) installing an indicator mechanism on the dispenser adjacent the second end to record the release of medication from the canister upon said applying an actuation force, the indicator mechanism including an indicator rotatable about and movable parallel to an axis of rotation, and a rotation mechanism for rotating the indicator about the axis of rotation upon the displacement of the canister in relation to the canister holder in the direction of said axis of rotation to move the indicator parallel to said axis of rotation; and (c) successively applying a force to the indicator mechanism to substantially simultaneously rotate the indicator and release medication.

22. The method of claim 21, wherein the step of installing an indicator mechanism includes attaching the indicator mechanism to the canister.

23. The method of claim 22, wherein said step of attaching the indicator mechanism includes press-fitting the indicator mechanism onto the canister.

24. The method of claim 22, wherein said step of attaching the indicator mechanism includes adhering the indicator mechanism to the canister.

25. The method of claim 21, wherein the indicator mechanism includes an actuator, a pawl on one of the actuator and the indicator and extending toward the other of the actuator and the indicator, and a set of pawl-engaging teeth on the other of the actuator and the indicator engaged with said pawl; and wherein said step of applying a force to the indicator mechanism includes flexing said pawl to drive the pawl-engaging teeth rotate the indicator in relation to the actuator.

26. The method of claim 25 wherein the actuator includes a first actuator member and a second actuator member limitedly moveable parallel to said axis of rotation in relation to the first actuator member, the indicator being positioned between said first actuator member and second actuator member; and wherein said step of applying a force to the indicator mechanism includes moving said second actuator member toward said first actuator member parallel to said axis of rotation.

27. The method of claims 26, wherein one of said first actuator member and said second actuator member includes a lug and the other of said first actuator member and said second actuator member includes a notch mated with the lug, the lug being limitedly shiftable in the notch substantially parallel to said axis of rotation; and wherein said step of moving said second actuator member toward said first actuator member includes shifting said lug in said notch.

28. A device to indicate the release of aerosol medication from a canister having a first end and a second end by applying a force to the canister in an axial direction, comprising: a dispenser including a canister case for holding the canister; and an indicator mechanism which rotates upon applying said force to indicate a release of the aerosol medication, the indicator mechanism mounting on the canister adjacent the second end; wherein the canister case includes an opening adjacent the first end to access said canister; and the indicator mechanism includes an indicator, an actuator engaged with the indicator to allow movement of the indicator in relation to the actuator, a set of indicia on at least one of the indicator and actuator to indicate the movement of the indicator in relation to the actuator, and a ratchet mechanism to limitedly move the indicator in relation to the actuator in a plane perpendicular to the axial direction upon application of a force applied in the axial direction to the actuator.

29. The device of claim 28, wherein the actuator includes a first actuator member and a second actuator member moveable with respect to the first actuator member, and the indicator mechanism further includes a biasing member urging apart the first actuator member and second actuator member; whereby the second actuator member moves in relation to the first actuator member and the indicator upon said application of force.

30. The device of claim 29, wherein the indicator is rotatable in relation to the actuator, said rotation being driven by the ratchet mechanism.

31. The device of claim 30, wherein said ratchet mechanism includes a flexible pawl on at least one of the indicator and actuator and extending toward the other of the indicator and actuator and a set of pawl-engaging teeth on the other of the indicator and actuator engaged with said pawl, whereby the movement of the actuator flexes the pawl to drive the teeth.

32. An indicator mechanism for use with a canister having an axis, comprising: an actuator having a first actuator member and a second actuator member having a means for engaging said canister; an indicator rotatively mounted between the first actuator member and second actuator member; a rotator for rotating the indicator in relation to said first actuator member in a first direction upon applying a non-rotative force to said first actuator member such that said first and second actuator members are moved axially towards each other, wherein the rotator includes a section that is flexed circumferentially with respect to the canister axis as the force is applied; a limiter for preventing rotation of the indicator in relation to said first actuator member in a second direction opposite the first direction upon release of said force; and indica to indicate the rotation of the indicator in relation to said first actuator member.

33. The mechanism of claim 32, wherein the rotator includes a pawl on one of the indicator and actuator and extending toward the other of the indicator and actuator and a set of pawl-engaging teeth on the other of the indicator and actuator engaged with the pawl whereby the movement of the actuator in relation to the indicator upon applying said force flexes the pawl to drive the pawl-engaging teeth to rotate the indicator in relation to the actuator.

34. The mechanism of claim 33, wherein the limiter includes at least one tooth on one of the indicator and actuator and a set of tooth-engaging teeth on the other of the indicator and actuator engaged with said tooth, the tooth and tooth-engaging teeth being configured such that rotation of the indicator in said first direction in relation to the actuator is allowed and rotation of the indicator in said second direction in relation to the actuator is prevented.

35. The mechanism of claim 33, further comprising a stop on one of the indicator and actuator and a mating stop on the other of the indicator and actuator to prevent rotation of the indicator mechanism in said first direction when the indicator rotates to a predetermined position in relation to the actuator.

36. The mechanism of claim 32, wherein the indicator includes a reset member to rotate the indicator in said first direction to a desired reset position in relation to the actuator by applying a rotative force to the indicator without applying said non-rotative force.

37. The mechanism of claim 36, wherein the indicia include a rotative start position of the indicator in relation to the actuator, and said reset member is adapted to rotate the indicator to said start position.

38. The mechanism of claim 37, wherein the reset member includes a hub extending axially from the indicator and through a hole in the actuator, the hub having an engager to engage for the rotation of the hub and indicator in relation to the actuator.

39. The mechanism of claim 38, wherein the engager includes a slot.

40. The mechanism of claim 32, wherein the mechanism is for use with a device for the administration of medication at predetermined times, and wherein the indicia include amount indicia corresponding to the amount of medication administered from said medication device and timing indicia to indicate the time of a past or future administration of medicine from the medication device.

41. The mechanism of claim 40, wherein the amount indicia includes a spiral line on the indicator and a spiral line window in the actuator for viewing the spiral line, whereby the rotation of the indicator in relation to the actuator produces the effect of radial movement of the spiral line in relation to the window.

42. The mechanism of claim 40 wherein the timing indicia include a set of alternating timing indica in the indicator and a timing indicia window in the actuator for viewing the timing indica, whereby successive rotation of the indicator in relation to the actuator alternates the timing indicia viewable through the timing indicia window.

43. The mechanism of claim 42, wherein the actuator includes at least two timing indicia windows for viewing timing indicia indicating at least two periodic times for administration of medication.

44. The mechanism of claim 43, wherein the actuator includes at least three timing indicia windows for viewing timing indicia indicating at least three periodic times for administration of medication.

* * * * *